United States Patent
Musselman

(10) Patent No.: US 10,090,142 B2
(45) Date of Patent: Oct. 2, 2018

(54) APPARATUS AND METHOD FOR SAMPLING OF CONFINED SPACES

(71) Applicant: IONSENSE INC., Saugus, MA (US)

(72) Inventor: Brian D Musselman, Melrose, MA (US)

(73) Assignee: IONSENSE, INC, Saugus, MA (US)

( * ) Notice: Subject to any disclaimer, the term of this patent is extended or adjusted under 35 U.S.C. 154(b) by 0 days.

(21) Appl. No.: 15/495,246

(22) Filed: Apr. 24, 2017

(65) Prior Publication Data

US 2017/0229299 A1    Aug. 10, 2017

Related U.S. Application Data

(63) Continuation of application No. 15/081,459, filed on Mar. 25, 2016, now Pat. No. 9,633,827, which is a
(Continued)

(51) Int. Cl.
*H01J 49/10* (2006.01)
*G01N 1/22* (2006.01)
(Continued)

(52) U.S. Cl.
CPC ............ *H01J 49/10* (2013.01); *G01N 1/2214* (2013.01); *G01N 1/2226* (2013.01);
(Continued)

(58) Field of Classification Search
USPC ............ 250/281, 282, 288, 423 R, 423, 429, 250/442.11; 73/23.2, 23.22, 23.25, 23.37;
(Continued)

(56) References Cited

U.S. PATENT DOCUMENTS 3,633,027 A    1/1972 Rhyage
3,957,470 A    5/1976 Dawes
(Continued)

FOREIGN PATENT DOCUMENTS

DE    102007015542    10/2007
EP    1434050    6/2004
(Continued)

OTHER PUBLICATIONS

The AccuTOF-DART Mass Spectrometer, Jan. 1, 2006, pp. 1-6; www.jeolusa.com/SERVICESUPPORT/ApplicationsResources/AnalyticalInstruments/Documents/Downloads/tabid/337/DMXModule/693/CommandCore_Download/Default.aspx?EntryId=171.
(Continued)

*Primary Examiner* — Bernard Souw
(74) *Attorney, Agent, or Firm* — Sci-Law Strategies, PC.

(57) ABSTRACT

In various embodiments of the invention, a cargo container can be monitored at appropriate time intervals to determine that no controlled substances have been shipped with the cargo in the container. The monitoring utilizes reactive species produced from an atmospheric analyzer to ionize analyte molecules present in the container which are then analyzed by an appropriate spectroscopy system. In an embodiment of the invention, a sorbent surface can be used to absorb, adsorb or condense analyte molecules within the container whereafter the sorbent surface can be interrogated with the reactive species to generate analyte species characteristic of the contents of the container.

20 Claims, 8 Drawing Sheets

Related U.S. Application Data continuation of application No. 14/493,231, filed on Sep. 22, 2014, now Pat. No. 9,390,899, which is a continuation of application No. 14/279,644, filed on May 16, 2014, now Pat. No. 8,895,916, which is a continuation of application No. 13/831,957, filed on Mar. 15, 2013, now Pat. No. 8,729,496, which is a continuation of application No. 13/530,387, filed on Jun. 22, 2012, now Pat. No. 8,563,945, which is a continuation of application No. 12/776,034, filed on May 7, 2010, now Pat. No. 8,207,497.

(60) Provisional application No. 61/176,860, filed on May 8, 2009.

(51) Int. Cl.
G01N 27/62 (2006.01)
H01J 49/00 (2006.01)
H01J 49/04 (2006.01)
G01N 1/02 (2006.01)

(52) U.S. Cl.
CPC ........... *G01N 1/2273* (2013.01); *G01N 27/62* (2013.01); *H01J 49/0027* (2013.01); *H01J 49/0409* (2013.01); *G01N 2001/022* (2013.01)

(58) Field of Classification Search
USPC ......... 422/244, 280, 906; 324/459, 464, 465
See application file for complete search history.

(56) References Cited

U.S. PATENT DOCUMENTS

| | | |
|---|---|---|
| 4,016,421 A | 4/1977 | Hull |
| 4,144,451 A | 3/1979 | Kambara |
| 4,213,326 A | 7/1980 | Brodasky |
| 4,542,293 A | 9/1985 | Fenn |
| 4,546,253 A | 10/1985 | Tsuchiya |
| 4,654,052 A | 3/1987 | Sharp |
| 4,662,914 A | 5/1987 | Hansen |
| 4,861,988 A | 8/1989 | Henion |
| 5,012,052 A | 4/1991 | Hayes |
| 5,055,677 A | 10/1991 | Amirav |
| 5,137,553 A | 8/1992 | Dawes |
| 5,192,865 A | 3/1993 | Zhu |
| 5,306,412 A | 4/1994 | Whitehouse |
| 5,352,892 A | 10/1994 | Mordehai |
| 5,367,163 A | 11/1994 | Otsuka |
| 5,381,008 A | 1/1995 | Tanner |
| 5,412,208 A | 5/1995 | Covey |
| 5,448,062 A | 9/1995 | Cooks |
| 5,552,599 A | 9/1996 | Giessmann |
| 5,559,326 A | 9/1996 | Goodley |
| 5,614,711 A | 3/1997 | Li |
| 5,624,537 A | 4/1997 | Turner |
| 5,684,300 A | 11/1997 | Taylor |
| 5,716,825 A | 2/1998 | Hancock |
| 5,736,741 A | 4/1998 | Bertsch |
| 5,788,166 A | 8/1998 | Valaskovic |
| 5,859,433 A | 1/1999 | Franzen |
| 5,868,322 A | 2/1999 | Loucks, Jr. |
| 5,877,495 A | 3/1999 | Takada |
| 5,889,404 A | 3/1999 | Abdel-Rahman |
| 5,959,297 A | 9/1999 | Weinberg |
| 5,997,746 A | 12/1999 | Valaskovic |
| 6,085,601 A | 7/2000 | Linker |
| 6,107,628 A | 8/2000 | Smith |
| 6,124,675 A | 9/2000 | Betrand |
| 6,190,559 B1 | 2/2001 | Valaskovic |
| 6,225,623 B1 | 5/2001 | Turner |
| 6,297,499 B1 | 10/2001 | Fenn |
| 6,359,275 B1 | 3/2002 | Bertsch |
| 6,395,183 B1 | 5/2002 | Valaskovic |
| 6,562,211 B1 | 5/2003 | Kunnecke |
| 6,583,408 B2 | 6/2003 | Smith |
| 6,600,155 B1 | 7/2003 | Andrien, Jr. |
| 6,646,256 B2 | 11/2003 | Gourley |
| 6,649,907 B2 | 11/2003 | Ebeling |
| 6,670,608 B1 | 12/2003 | Taylor |
| 6,690,006 B2 | 2/2004 | Valaskovic |
| 6,713,757 B2 | 3/2004 | Tanner |
| 6,717,139 B2 | 4/2004 | Taniguchi |
| 6,723,985 B2 | 4/2004 | Schultz |
| 6,744,041 B2 | 6/2004 | Sheehan |
| 6,744,046 B2 | 6/2004 | Valaskovic |
| 6,753,523 B1 | 6/2004 | Whitehouse |
| 6,784,424 B1 | 8/2004 | Willoughby |
| 6,794,642 B2 | 9/2004 | Bateman |
| 6,803,565 B2 | 10/2004 | Smith |
| 6,806,468 B2 | 10/2004 | Laiko |
| 6,818,889 B1 | 11/2004 | Sheehan |
| 6,861,647 B2 | 3/2005 | Reilly |
| 6,875,980 B2 | 4/2005 | Bateman |
| 6,878,930 B1 | 4/2005 | Willoughby |
| 6,888,132 B1 | 5/2005 | Sheehan |
| 6,914,243 B2 | 7/2005 | Sheehan |
| 6,943,347 B1 | 9/2005 | Willoughby |
| 6,949,739 B2 | 9/2005 | Franzen |
| 6,949,740 B1 | 9/2005 | Sheehan |
| 6,949,741 B2 | 9/2005 | Cody |
| 6,956,205 B2 | 10/2005 | Park |
| 6,977,372 B2 | 12/2005 | Valaskovic |
| 6,979,816 B2 | 12/2005 | Tang |
| 6,987,264 B1 | 1/2006 | Whitehouse |
| 6,992,299 B2 | 1/2006 | Lee |
| 7,015,466 B2 | 3/2006 | Takats |
| 7,019,289 B2 | 3/2006 | Wang |
| 7,034,292 B1 | 4/2006 | Whitehouse |
| 7,041,972 B2 | 5/2006 | Bajic |
| 7,049,584 B1 | 5/2006 | Whitehouse |
| 7,053,368 B2 | 5/2006 | Thakur |
| 7,064,317 B2 | 6/2006 | McLuckey |
| 7,071,464 B2 | 7/2006 | Reinhold |
| 7,081,618 B2 | 7/2006 | Laprade |
| 7,081,621 B1 | 7/2006 | Willoughby |
| 7,095,019 B1 | 8/2006 | Sheehan |
| 7,098,452 B2 | 8/2006 | Schneider |
| 7,112,785 B2 | 9/2006 | Laramee |
| 7,138,626 B1 | 11/2006 | Karpetsky |
| 7,157,698 B2 | 1/2007 | Makarov |
| 7,161,145 B2 | 1/2007 | Oser |
| 7,196,525 B2 | 3/2007 | Sparkman |
| 7,247,495 B2 | 7/2007 | Amirav |
| 7,253,406 B1 | 8/2007 | Sheehan |
| 7,332,345 B2 | 2/2008 | Darrach |
| 7,423,261 B2 | 9/2008 | Truche |
| 7,429,731 B1 | 9/2008 | Karpetsky |
| 7,462,826 B2 | 12/2008 | Schneider |
| 7,544,933 B2 | 6/2009 | Cooks |
| 7,569,812 B1 | 8/2009 | Karpetsky |
| 7,582,864 B2 | 9/2009 | Verentchikov |
| 7,700,913 B2 | 4/2010 | Musselman |
| 7,705,297 B2 | 4/2010 | Musselman |
| 7,714,281 B2 | 5/2010 | Musselman |
| 7,772,546 B2 | 8/2010 | Jackson |
| 7,777,181 B2 | 8/2010 | Musselman |
| 7,858,926 B1 | 12/2010 | Whitehouse |
| 7,893,408 B2 | 2/2011 | Hieftje |
| 7,915,579 B2 | 3/2011 | Chen |
| 7,923,681 B2 | 4/2011 | Collings |
| 7,928,364 B2 | 4/2011 | Musselman |
| 7,929,138 B1 | 4/2011 | Webb |
| 7,982,183 B2 | 7/2011 | Marakov |
| 7,982,185 B2 | 7/2011 | Whitehouse |
| 8,003,935 B2 | 8/2011 | Robinson |
| 8,026,477 B2 | 9/2011 | Musselman |
| 8,044,346 B2 | 10/2011 | Kostiainen |
| RE43,078 E | 1/2012 | Cody |
| 8,101,910 B2 | 1/2012 | Loboda |
| 8,207,497 B2 * | 6/2012 | Musselman ............ H01J 49/10 250/281 |
| 8,217,341 B2 | 7/2012 | Musselman |
| 8,242,459 B2 | 8/2012 | Sun |

(56) References Cited

U.S. PATENT DOCUMENTS

| | | | |
|---|---|---|---|
| 8,278,619 B2 | 10/2012 | Makarov | |
| 8,304,718 B2 | 11/2012 | Ouyang | |
| 8,308,339 B2 | 11/2012 | Karpetsky | |
| 8,334,507 B1 | 12/2012 | Whitehouse | |
| 8,362,418 B2 | 1/2013 | Xu | |
| 8,410,431 B2 | 4/2013 | Ouyang | |
| 8,421,005 B2 | 4/2013 | Musselman | |
| 8,440,965 B2 | 5/2013 | Musselman | |
| 8,481,922 B2 | 7/2013 | Musselman | |
| 8,497,474 B2 | 7/2013 | Musselman | |
| 8,519,354 B2 | 8/2013 | Charipar | |
| 8,525,109 B2 | 9/2013 | Musselman | |
| 8,563,945 B2 * | 10/2013 | Musselman | H01J 49/10 250/288 |
| RE44,603 E | 11/2013 | Cody | |
| 8,592,756 B2 | 11/2013 | Ouyang | |
| 8,592,758 B1 | 11/2013 | Nilles | |
| 8,604,423 B2 | 12/2013 | Enke | |
| 8,648,295 B2 | 2/2014 | Enke | |
| 8,664,000 B2 | 3/2014 | Yang | |
| 8,686,351 B2 | 4/2014 | Ouyang | |
| 8,704,167 B2 | 4/2014 | Cooks | |
| 8,710,437 B2 | 4/2014 | Cooks | |
| 8,729,496 B2 * | 5/2014 | Musselman | H01J 49/10 250/281 |
| 8,754,365 B2 | 6/2014 | Krechmer | |
| 8,766,178 B2 | 7/2014 | Ouyang | |
| 8,803,085 B2 | 8/2014 | Ouyang | |
| 8,816,275 B2 | 8/2014 | Ouyang | |
| 8,822,949 B2 | 9/2014 | Musselman | |
| 8,853,627 B2 | 10/2014 | Ouyang | |
| 8,859,956 B2 | 10/2014 | Ouyang | |
| 8,859,957 B2 | 10/2014 | Ouyang | |
| 8,859,958 B2 | 10/2014 | Ouyang | |
| 8,859,959 B2 | 10/2014 | Ouyang | |
| 8,890,063 B2 | 11/2014 | Ouyang | |
| 8,895,916 B2 * | 11/2014 | Musselman | H01J 49/10 250/281 |
| 8,895,918 B2 | 11/2014 | Cooks | |
| 8,927,926 B2 | 1/2015 | Shimada | |
| 8,932,875 B2 | 1/2015 | Cooks | |
| 8,933,398 B2 | 1/2015 | Ouyang | |
| 8,937,288 B1 | 1/2015 | Cooks | |
| 8,963,079 B2 | 2/2015 | Ouyang | |
| 8,963,101 B2 | 2/2015 | Krechmer | |
| 9,024,254 B2 | 5/2015 | Cooks | |
| 9,064,674 B2 | 6/2015 | Ouyang | |
| 9,105,435 B1 | 8/2015 | Musselman | |
| 9,116,154 B2 | 8/2015 | Ouyang | |
| 9,159,540 B2 | 10/2015 | Ouyang | |
| 9,165,752 B2 | 10/2015 | Cooks | |
| 9,224,587 B2 | 12/2015 | Musselman | |
| 9,230,792 B2 | 1/2016 | Cooks | |
| 9,337,007 B2 | 5/2016 | Musselman | |
| 9,390,899 B2 * | 7/2016 | Musselman | H01J 49/10 |
| 9,484,195 B2 | 11/2016 | Ouyang | |
| 9,500,630 B2 | 11/2016 | Cooks | |
| 9,514,923 B2 | 12/2016 | Krechmer | |
| 9,538,945 B2 | 1/2017 | Cooks | |
| 9,546,979 B2 | 1/2017 | Cooks | |
| 9,548,192 B2 | 1/2017 | Cooks | |
| 9,551,079 B2 | 1/2017 | Cooks | |
| 9,558,926 B2 | 1/2017 | Musselman | |
| 9,607,306 B2 | 3/2017 | Hieftje | |
| RE46,366 E | 4/2017 | Cody | |
| 9,620,344 B2 | 4/2017 | Cooks | |
| 9,633,827 B2 * | 4/2017 | Musselman | H01J 49/10 |
| 9,700,251 B2 | 7/2017 | Cooks | |
| 9,704,700 B2 | 7/2017 | Cooks | |
| 9,719,181 B2 | 8/2017 | Cooks | |
| 9,733,228 B2 | 8/2017 | Cooks | |
| 2002/0121596 A1 | 9/2002 | Laiko | |
| 2002/0121598 A1 | 9/2002 | Park | |
| 2002/0162967 A1 | 11/2002 | Atkinson | |
| 2002/0185593 A1 | 12/2002 | Doring | |
| 2002/0185595 A1 | 12/2002 | Smith | |
| 2002/0185606 A1 | 12/2002 | Smith | |
| 2003/0052268 A1 | 3/2003 | Doroshenko | |
| 2004/0094706 A1 | 5/2004 | Covey | |
| 2004/0129876 A1 | 7/2004 | Franzen | |
| 2004/0159784 A1 | 8/2004 | Doroshenko | |
| 2005/0230635 A1 | 10/2005 | Takats | |
| 2005/0236374 A1 | 10/2005 | Blankenship | |
| 2006/0266941 A1 | 11/2006 | Vestal | |
| 2007/0114389 A1 | 5/2007 | Karpetsky | |
| 2007/0228271 A1 | 10/2007 | Truche | |
| 2008/0156985 A1 | 7/2008 | Venter | |
| 2008/0202915 A1 | 8/2008 | Hieftje | |
| 2008/0217254 A1 | 9/2008 | Anderson | |
| 2009/0090858 A1 | 4/2009 | Musselman | |
| 2010/0078550 A1 | 4/2010 | Wiseman | |
| 2010/0140468 A1 | 6/2010 | Musselman | |
| 2010/0294925 A1 * | 11/2010 | Musselman | H01J 49/10 250/282 |
| 2011/0215798 A1 | 9/2011 | Beer | |
| 2012/0006983 A1 | 1/2012 | Cody | |
| 2012/0145890 A1 | 6/2012 | Goodlett | |
| 2012/0208004 A1 | 8/2012 | Wolcott | |
| 2012/0223226 A1 | 9/2012 | Rafferty | |
| 2012/0280119 A1 * | 11/2012 | Musselman | H01J 49/10 250/282 |
| 2012/0312980 A1 | 12/2012 | Whitehouse | |
| 2012/0322683 A1 | 12/2012 | Liu | |
| 2013/0020482 A1 | 1/2013 | Enke | |
| 2013/0037710 A1 | 2/2013 | Wu | |
| 2013/0092832 A1 | 4/2013 | Enke | |
| 2013/0273552 A1 | 10/2013 | Ohashi | |
| 2013/0284915 A1 | 10/2013 | Shimada | |
| 2014/0024822 A1 | 1/2014 | Connolly | |
| 2016/0314956 A1 | 10/2016 | Cooks | |
| 2017/0082604 A1 | 3/2017 | Ouyang | |
| 2017/0084438 A1 | 3/2017 | Cooks | |
| 2017/0103879 A1 | 4/2017 | Cooks | |
| 2017/0130352 A1 | 5/2017 | Cooks | |
| 2017/0135613 A1 | 5/2017 | Cooks | |
| 2017/0148622 A1 | 5/2017 | Musselman | |
| 2017/0154761 A1 | 6/2017 | Ouyang | |
| 2017/0168032 A1 | 6/2017 | Cooks | |
| 2017/0221695 A1 | 8/2017 | Cooks | |
| 2017/0229299 A1 | 8/2017 | Musselman | |
| 2017/0248607 A1 | 8/2017 | Cooks | |
| 2017/0273605 A1 | 9/2017 | Cooks | |
| 2017/0287690 A1 | 10/2017 | Cooks | |
| 2017/0309462 A1 | 10/2017 | Cooks | |

FOREIGN PATENT DOCUMENTS

| | | |
|---|---|---|
| GB | 2263578 | 7/1993 |
| JP | 50-106694 | 8/1975 |
| JP | 51-120288 | 10/1976 |
| JP | 52-91494 | 8/1977 |
| JP | 60-41748 | 3/1985 |
| JP | 2003185635 | 7/2003 |
| JP | 2003222574 | 8/2003 |
| JP | 2005-150027 | 6/2005 |
| JP | 2007525677 | 6/2007 |
| JP | 2009539114 | 11/2009 |
| WO | WO03025973 | 3/2003 |
| WO | WO03081205 | 10/2003 |
| WO | WO2004068131 | 8/2004 |
| WO | WO2005094389 | 10/2005 |
| WO | WO2008054393 | 5/2008 |
| WO | WO2008082603 | 7/2008 |
| WO | WO2015195599 | 12/2015 |
| WO | WO2016145041 | 9/2016 |
| WO | WO2017040359 | 3/2017 |
| WO | WO2017053911 | 3/2017 |
| WO | WO2017070478 | 4/2017 |
| WO | WO2017079193 | 5/2017 |
| WO | WO2017127670 | 7/2017 |

(56) References Cited

FOREIGN PATENT DOCUMENTS

| WO | WO2017132444 | 8/2017 |
|---|---|---|
| WO | WO2017180871 | 10/2017 |

OTHER PUBLICATIONS

Cody, R.B. et al., "Versatile New Ion Source for the Analysis of Materials in Open Air under Ambient Conditions" Anal. Chem., 2005, 77, 2297-2302.
Cooks, R.G. et al., "Ambient Mass Spectrometry", Science, 2006, 311, 1566-1570.
Dalton, C.N. et al., "Electrospray-Atmospheric Sampling Glow Discharge Ionization Source for the Direct Analysis of Liquid Samples", Analytical Chemistry, Apr. 1, 2003, vol. 75, No. 7, pp. 1620-1627.
Garimella, S. et al., "Gas-flow assisted ion transfer for mass spectrometry", J. Mass Spectrom. 2012, 17, 201-207.
Guzowski, J.P. Jr. et al., "Development of a Direct Current Gas Sampling Glow Discharge Ionization Source for the Time-of-Flight Mass Spectrometer", J. Anal. At. Spectrom., 14, 1999, pp. 1121-1127.
Haddad, R., et al., "Easy Ambient Sonic-Spray Ionization Mass Spectrometry Combined with Thin-Layer Chromatography," *Analytical Chemistry*, vol. 80, No. 8, Apr. 15, 2008, pp. 2744-2750.
Harris, Glenn A. et al., Ambient Sampling/Ionization Mass Spectrometry: Applications and Current Trends, Apr. 15, 2011, Anal. Chem. 2011, 83, pp. 4508-4538.
Harris, Glenn A. et al., Simulations and Experimental Investigation of Atmospheric Transport in an Ambient Metastable-Induced Chemical Ionization Source, Anal. Chem. 2009, 81, pp. 322-329.
Hill, C.A. et al., "A pulsed corona discharge switchable high resolution ion mobility spectrometer-mass spectrometer", Analyst, 2003, 128, pp. 55-60.
Hiraoka, K. et al., "Atmospheric-Pressure Penning Ionization Mass Spectrometry", Rapid Commun. Mass Spectrom., 18, 2004, pp. 2323-2330.
McLuckey, S.A. et al., "Atmospheric Sampling Glow Discharge Ionization Source for the Determination of Trace Organic Compounds in Ambient Air", Anal. Chem., 60, 1988, pp. 2220-2227.
Otsuka, K. et al., "An Interface for Liquid Chromatograph/Liquid Ionization Mass Spectrometer", Analytical Sciences, Oct. 1988, vol. 4, pp. 467-472.
Takáts et al., "Mass Spectrometry Sampling Under Ambient Conditions with Desorption Electrospray Ionization," Science, vol. 306, No. 5695, Oct. 15, 2004, pp. 471-473.
Tembreull, R., et al., "Pulsed Laser Desorption with Resonant Two-Photon Ionization Detection in Supersonic Beam Mass Spectrometry," Anal. Chem., vol. 58, 1986, pp. 1299-1303, p. 1299.
Zhao, J. et al., Liquid Sample Injection Using an Atmospheric Pressure Direct Current Glow Discharge Ionization Source, Analytical Chemistry, Jul. 1, 1992, vol. 64, No. 13, pp. 1426-1433.
International Search Report, Application No. PCT/US2007/63006, dated Feb. 5, 2008, 8 pages.
Extended European Search Report, Application No. 07757665.0 PCT/US2007/063006 dated Jan. 7, 2010, 8 pages.
Article 94(3) European Communication, Application No. 07757665.0 PCT/US2007/063006, dated Mar. 14, 2012, 9 pages.
International Search Report, Application No. PCT/US2007/69823, dated Feb. 15, 2008, 8 pages.
Extended European Search Report, Application No. 07797812.0 PCT/US2007/069823, dated Apr. 4, 2010, 9 pages.
Article 94(3) European Communication, Application No. 07797812.0 PCT/US2007/069823, dated Jul. 27, 2012, 9 pages.
International Search Report, Application No. PCT/US2007/69821, dated Feb. 7, 2008.
Extended European Search Report, Application No. 07797811.2 PCT/US2007/069821, dated Mar. 25, 2010, 9 pages.
European Summons, Application No. 07797811.2 PCT/US2007/069821, Feb. 18, 2013, 8 pages.
International Search Report, Application No. PCT/US2007/81439, dated Mar. 20, 2008, 9 pages.
Extended European Search Report, Application No. 07844307.4 PCT/US2007/081439, dated Apr. 14, 2010, 12 pages.
Japanese Office Action, Application No. 2008-558459 PCT/US2007/063006, dated Jan. 19, 2012, 4 pages.
Unofficial Translation of Japanese Office Action, Application No. 2008-558459 PCT/US2007/063006, dated Jan. 19, 2012, 5 pages.
Chinese Office Action, Application No. 200780015974.5 PCT/US2007/063006, dated Feb. 2, 2012, 5 pages.
Chinese Office Action, Application No. 200780015974.5 PCT/US2007/063006, dated Sep. 25, 2012, 8 pages.
Chinese Office Action, Application No. 200780015974.5 PCT/US2007/063006, dated Dec. 26, 2012, 7 pages.
International Search Report, Application No. PCT/US2012/000061, dated Aug. 6, 2013, 8 pages.
Oral Proceedings European Communication, Application No. 07757665.0 PCT/US2007/063006, Sep. 3, 2013, 5 pages.
Korean Patent Application 7024130/2008 Office Action, dated Jun. 29, 2013, 3 pages.
Korean Patent Application 7024130/2008 Office Action, translation, dated Jun. 29, 2013, 3 pages.
Article 94(3) European Communication, Application No. 07797811.2 PCT/US2007/069821, dated Feb. 2, 2012, 8 pages.
Summons Application No. 07797811.2 PCT/US2007/069821, Feb. 18, 2013, 10 pages.
Chinese Office Action, Application No. 201280003101.3 PCT/US12/00061, dated Jan. 22, 2016, 3 pages.
Translation of Chinese Office Action, Application No. 201280003101.3 PCT/US12/00061, dated Jan. 22, 2016, 18 pages.
Japanese Office Action, Application No. 2013552527 PCT/US12/00061, dated Jan. 22, 2016, 3 pages.
Translation of Japanese Office Action, Application No. 2013552527 PCT/US12/00061, dated Jan. 22, 2016, 4 pages.
Extended European Search Report, Application No. 12742544.5 PCT/US20012/0000061, dated Sep. 12, 2017, 9 pages.
Gibbons, J.R., 'Variable Heating Rate Wire Mesh Pyrolysis Apparatus' Rev. Sci. Instr. 60 (1989) pp. 1129-1139.

\* cited by examiner

APPARATUS AND METHOD FOR SAMPLING OF CONFINED SPACES

CLAIM OF PRIORITY

The present application is a continuation of and claims priority to (1) U.S. patent application Ser. No. 15/081,459 entitled "APPARATUS AND METHOD FOR SAMPLING OF CONFINED SPACES" by Inventor Brian D. Musselman, filed Mar. 25, 2016; which is a continuation of and claims priority to (2) U.S. patent application Ser. No. 14/493,231 entitled "APPARATUS AND METHOD FOR SAMPLING OF CONFINED SPACES" by Inventor Brian D. Musselman, filed Sep. 22, 2014 which issued Jul. 12, 2016 as U.S. Pat. No. 9,390,899; which is a continuation of and claims priority to (3) U.S. patent application Ser. No. 14/279,644 entitled "APPARATUS AND METHOD FOR SAMPLING OF CONFINED SPACES" by Inventor Brian D. Musselman, filed May 16, 2014, which issued Nov. 25, 2014 as U.S. Pat. No. 8,895,916; which is a continuation of and claims priority to (4) U.S. patent application Ser. No. 13/831,957 entitled "APPARATUS AND METHOD FOR SAMPLING OF CONFINED SPACES" by Inventor Brian D. Musselman, filed Mar. 15, 2013, which issued May 20, 2014 as U.S. Pat. No. 8,729,496; which is a continuation of and claims priority to (5) U.S. patent application Ser. No. 13/530,387 entitled "SAMPLING OF CONFINED SPACES" by Inventor Brian D. Musselman, filed Jun. 22, 2012, which issued Oct. 22, 2013 as U.S. Pat. No. 8,563,945; which is a continuation of and claims priority to (6) U.S. patent application Ser. No. 12/776,034 entitled "SAMPLING OF CONFINED SPACES" by Inventor Brian D. Musselman, filed May 7, 2010, which issued Jun. 26, 2012 as U.S. Pat. No. 8,207,497; which claims priority to (7) U.S. Provisional Patent Application No. 61/176,860 entitled "MATERIAL COLLECTOR AND PORTABLE IONIZER FOR REMOTE SAMPLING OF CONFINED SPACES" by Inventor Brian D. Musselman, filed May 8, 2009, the contents of each of (1)-(7) are incorporated herein by reference in their entireties.

CROSS-REFERENCE TO RELATED APPLICATIONS

This application is related to the following applications: (8) U.S. Utility patent application Ser. No. 11/580,323, entitled "A SAMPLING SYSTEM FOR USE WITH SURFACE IONIZATION SPECTROSCOPY" by Brian D. Musselman, filed Oct. 13, 2006 which issued Apr. 20, 2010 as U.S. Pat. No. 7,700,913;
(9) U.S. Utility patent application Ser. No. 11/754,115, entitled "HIGH RESOLUTION SAMPLING SYSTEM FOR USE WITH SURFACE IONIZATION TECHNOLOGY" by Brian D. Musselman, filed May 25, 2007, which issued Aug. 17, 2010 as U.S. Pat. No. 7,777,181;
(10) U.S. Utility patent application Ser. No. 11/754,158, entitled "APPARATUS FOR HOLDING SOLIDS FOR USE WITH SURFACE IONIZATION TECHNOLOGY" by Brian D. Musselman, filed May 25, 2007 which issued May 11, 2010 as U.S. Pat. No. 7,714,281;
(11) U.S. Utility patent application Ser. No. 11/754,189, entitled "FLEXIBLE OPEN TUBE SAMPLING SYSTEM FOR USE WITH SURFACE IONIZATION TECHNOLOGY" by Brian D. Musselman, filed May 25, 2007 which issued Apr. 27, 2010 as U.S. Pat. No. 7,705,297;
(12) U.S. Utility patent application Ser. No. 11/872,666, entitled "SAMPLING SYSTEM FOR CONTAINMENT AND TRANSFER OF IONS INTO A SPECTROSCOPY SYSTEM" by Brian D. Musselman, filed Oct. 15, 2007, which issued Apr. 19, 2011 as U.S. Pat. No. 7,928,364; and
(13) U.S. Utility patent application Ser. No. 12/275,079, entitled "SAMPLING SYSTEM FOR USE WITH SURFACE IONIZATION SPECTROSCOPY" by Brian D. Musselman, filed Nov. 20, 2008, which issued Sep. 27, 2011 as U.S. Pat. No. 8,026,477.

These related applications (8)-(13) are herein expressly incorporated by reference in their entireties.

FIELD OF THE INVENTION

The present invention relates to rapid, remote sampling of analyte ions in confined spaces.

BACKGROUND OF THE INVENTION

A shipping container can be used for transporting machinery, equipment and produce. They are designed and built to carry heavy loads and support heavy loads, even when they are stacked on top of each other. They tolerate harsh environments when they are transported globally. Most shipping containers are made to the same standard measurements (8' width, 20', 35', 40' or 45' length and 8'6" or 9'6" height). They can include top, side and bottom rails with interval stringers in between the top and bottom rails and doors at one end. As many as 30 interval stringers can be present in a 40' container to help prevent delamination of the outer container coating from the container frame. As a result the containers can be structurally very strong and when empty can be stacked upon each other up to twelve high.

A drum, or more specifically a 55-gallon drum (or 44-gallon drum based on the imperial volume) is another commonly used container for shipping materials. A 55-gallon drum is 22.5 inches (572 mm) in diameter and 33.5 inches (851 mm) high as specified in ANSI MH2 and has a volume of approximately 208-liters. A 42 gallon (159 liter) and 25 gallon (95 liter) drum are also common size containers used for shipping. A drum shipping container can be closed-head or open-head. Closed-head drums are generally made of a steel cylinder with reinforcing rings to improve rigidity and durability. Bottom and top plates can be welded to the cylinder. The reinforcing rings are positioned at the bottom, one third, two thirds and top. The top plate has one 2-inch (50.8 mm) NPT and one ¾-inch (19 mm) NPT threaded holes or bungs. These are generally on opposite sides. This arrangement is echoed in many plastic drums of the same size. Various components can be mounted to the drum, such as drum pumps and bung mixers. They are commonly used for transporting oils, fuels and a variety of chemicals. Open-head drums are sealed by a concave inwards mechanical ring clamp that can make an airtight seal against a gasket. Top plates exist with standard bung holes. Open-head drums can be used to ship many non-volatile liquids as well as industrial powders (e.g., aluminum), beads (e.g., polystyrene) and granules (e.g., fertilizers).

SUMMARY OF THE INVENTION

The rapid determination of the composition of an analyte inside a confined container and in particular a shipping container is of interest to national security. In various embodiments of the invention, a container can be monitored at appropriate time intervals to determine whether any and which controlled substances have been shipped in the container. In an embodiment of the invention, a sorbent surface can be used to sample the contents of the container and an atmospheric analyzer can be used to ionize analyte species (AS) including molecules or fragments present on the sorbent surface which are then analyzed by an appropriate spectroscopy system.

In an embodiment of the invention, a sorbent surface can be used to absorb, adsorb or condense analyte molecules within the container where after the sorbent surface can be interrogated with the reactive species (RS) to generate analyte species (AS) characteristic of the contents of the container. In an embodiment of the invention, a plurality of sorbent materials located in a container can be simultaneously and/or sequentially exposed to the atmosphere in the container and absorb, adsorb or condense analyte molecules onto the sorbent surface, where the analyte molecules are characteristic of the contents of the container. In various embodiments of the invention, movement of the air within the container to either an area where the RS are present or to the sorbent material can be facilitated. Over an interval of time, the sorbent material can be subjected to analysis either while fixed in situ and/or after removal of the sorbent material. Analysis can include exposure of the sorbent material to RS produced by an atmospheric ionizer in order to ionize the analyte molecules present on the sorbent material generating AS and then transfer of the AS to a spectroscopic analysis and detection system.

BRIEF DESCRIPTION OF THE DRAWINGS

Various embodiments of the present invention will be described in detail based on the following figures, wherein.

DETAILED DESCRIPTION OF THE INVENTION

Figure 1:
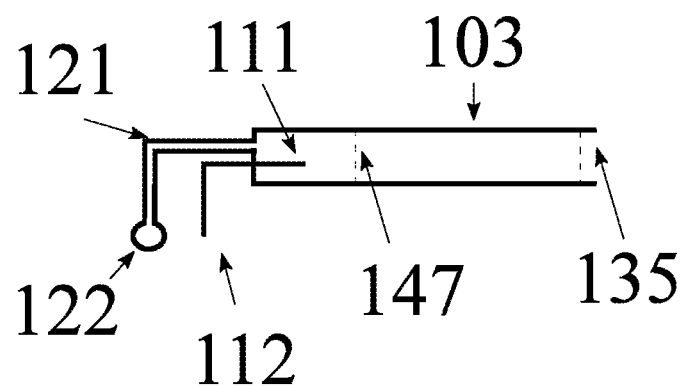
FIG. 1 is a schematic diagram of an atmospheric ionizer in which the entrance is closed for analysis.

Abbreviations include:
AISM=atmospheric ionization sorbent material; API=atmospheric pressure ionization; AS=analyte species; DESI=desorption electrospray ionization; DMS=differential mobility spectrometer; GIS=gas ion separator; IMS=ion mobility spectrometer; MS=mass spectrometry; RS=reactive species.

Definitions of certain terms that are used hereinafter include:

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The term Gas-Ion Separator (GIS) will be used to refer to a device which separates ions from one or both neutral molecules and neutral atoms allowing the pre-concentration and transfer of the ions to an analysis system. The term 'inlet tube' will be used to refer to the low vacuum side of a GIS. The term 'outlet tube' will be used to refer to the high vacuum side of the GIS. The term 'contained tube' will be used to refer to a tube present in the container (that can be concealed) that normally functions to sample the atmosphere at different locations in the container. In various embodiments of the invention, the contained tube can be an inlet tube. Active ionization refers to the process where an atmospheric analyzer not utilizing a radioactive nucleus can be used to ionize analyte ions. Passive ionization refers to any process where a radioactive nuclei results in analyte ions. A capacitive surface is a surface capable of being charged with a potential. A surface is capable of being charged with a potential, if a potential applied to the surface remains for the typical duration time of an experiment, where the potential at the surface is greater than 50% of the potential applied to the surface. A vacuum of atmospheric pressure is approximately 760 torr. Generally, 'approximately' in this pressure range encompasses a range of pressures from below $10^1$ atmosphere=$7.6 \times 10^3$ torr to $10^{-1}$ atmosphere=$7.6 \times 10^1$ torr. A vacuum of below $10^{-3}$ torr would constitute a high vacuum. Generally, 'approximately' in this pressure range encompasses a range of pressures from below $5 \times 10^{-3}$ torr to $5 \times 10^{-6}$ torr. A vacuum of below $10^{-6}$ torr would constitute a very high vacuum. Generally, 'approximately' in this pressure range encompasses a range of pressures from below $5 \times 10^{-6}$ torr to $5 \times 10^{-9}$ torr. In the following, the phrase 'high vacuum' encompasses high vacuum and very high vacuum.

Cargo is any product to be shipped. Shipping means any transportation of a container including by ship, by plane, by space craft, by rail, by truck and by car. Loading a cargo includes placing, filling or dispensing a cargo in a container. Closing a container includes non-air tight sealing and air tight sealing. En route analysis includes any analysis of the AISM or the sorbent surface after the cargo has been loaded but before the cargo has been unloaded. Delivery means the arrival of the cargo container at any destination port and/or intermediate port. Port means any destination location. Unloading cargo means any removal of the cargo from the container. Initiation means any process that allows the prior exposure of the AISM to be substantially reduced or eliminated.

A. Active Ionization
DESI

Desorption ElectroSpray Ionization (DESI) is an atmospheric ionizer of analytes. DESI occurs when a gas under high pressure is use to project a stream of highly charged liquid particles onto a surface in order to desorb ions at atmospheric pressure into the space above the surface. Thus, DESI utilizes a liquid to complete the desorption ionization. The desorbed ions can be pulled into the vacuum envelope of a mass spectrometer inlet for subsequent mass determination or ion mobility determination. In these circumstances, the transfer of ions into the inlet of the MS relies in large part on the action of the vacuum to draw the ions into the MS inlet. MS sources often contain multiple pumping stages separated by small orifices, which serve to reduce the gas pressure along the path that the ions of interest travel to an acceptable level for mass analysis; these orifices also operate as ion focusing lenses when an electrical potential is applied to their surface.

DART®

DART® is another atmospheric ionization method suitable for the analysis of analytes. Various embodiments of DART® are described in U.S. Pat. No. 7,112,785 to Laramee (hereinafter referred to as the '785 patent) which are herein expressly incorporated by reference in their entireties. The '785 patent is directed to desorption ionization of molecules from surfaces, liquids and vapor using a carrier gas containing reactive species (RS). The DART® atmospheric ionizer can use a large volume of carrier gas, e.g., helium is suitable although other inert gases that can generate RS can be used.

Nitrogen DART

An atmospheric ionizer can ionize analyte molecules without the use of solvents to dissolve the analyte. The ionization occurs directly from solids and liquids. Molecules present in the gas phase can also be ionized by the reactive species exiting the atmospheric ionizer. In an embodiment of the invention, the reactive species utilized can be excited nitrogen atoms or molecules. In an embodiment of the invention, the reactive species can produce long lived metastables to impact the analyte molecules at atmospheric pressure and effect ionization.

The recent commercialization of a DART® atmospheric ionizer with increased capability for functioning with naturally abundant nitrogen as the metastable carrier gas is a significant advance. This can enable the utilization of the DART® atmospheric ionizer in more diverse climates, and with minimal requirement for compressed gases or any liquids commonly used with alternative atmospheric ionization systems. In an embodiment of the invention, processing of ambient air to remove the oxygen can be accomplished by placing a tube containing an oxygen scavenger in the path of gas flow from the air to the inlet of the DART® atmospheric ionizer. An oxygen absorbent (see U.S. Pat. No. 4,127,503 to Yoshikawa et al., which is incorporated by reference in its entirety) such as a mixture of finely divided moist $Fe_2O_3$ and KCl can be used to reduce the level of oxygen present in an air stream. In an alternative embodiment of the invention, a process for separating air by cryogenic distillation (U.S. Pat. No. 7,219,514 to Garnier et al., which is incorporated by reference in its entirety) using an apparatus comprising a medium-pressure column and a low-pressure column that are thermally coupled, where a quantity of compressed and purified air is cooled in an exchange line down to a cryogenic temperature and is sent at least partly to the medium-pressure column, and a nitrogen-enriched stream is sent from the medium-pressure column to the low-pressure column and the nitrogen-enriched stream can be withdrawn from the low-pressure column. In another embodiment of the invention, an oxygen absorbent can be used in combination with cryogenic distillation to further reduce the level of oxygen present in the nitrogen-enriched stream or more efficiently reduce the level of oxygen. An atmospheric ionizer therefore can be an ideal device for sampling of confined spaces into which introduction of solvents to mix with analytes might create an unstable chemical condition.

Sampling Different Areas and Compartments

Figure 5:
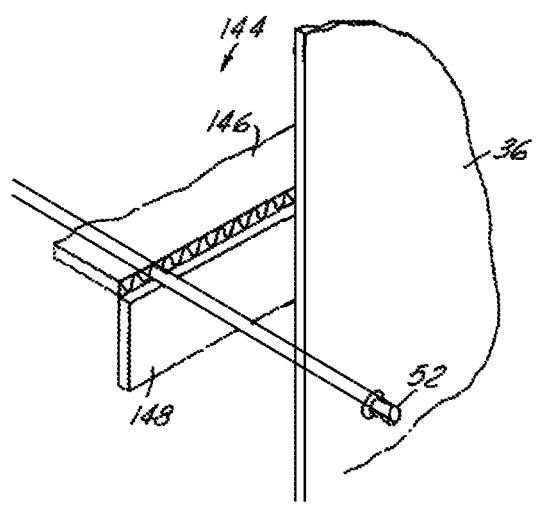
FIG. 5 is a schematic diagram of the containment tube according to an embodiment of the invention.

As shown in FIG. 5, in various embodiments of the invention, one or more containment tubes are used to allow diverse and/or large volumes of the container to be sampled. The proximal end of the containment tube 52 is closest to the position being sampled and the distal end of the containment tube 52 can be directed onto the sorbent surface (not shown). In FIG. 5, the containment tube 52 spans a partition 36 separating compartments in the container 144 by passing through the sub floor 146 above the sub floor support 148 of the container 144. In various embodiments of the invention, by embedding the containment tube into the container during construction of the container, the possibility of tampering with or otherwise interfering with the detection system can be reduced. In addition to a sub floor, a shipping container can contain a number of structural features including top, side and bottom rails with interval stringers in between the top and bottom rails and doors at one end. As many as 30 interval stringers can be present in a 40'. A shipping drum can also contain a number of structural features including reinforcing rings positioned at the bottom, one third, two thirds and top. In addition, a shipping container in the shape of a drum generally contains a seam running from the bottom plate to the top plate.

In an embodiment of the invention, the containment tubing can be made of one or more materials selected from the group consisting of stainless steel, non-magnetic stainless steel, steel, titanium, metal, flexible metal, ceramic, silica glass, plastic and flexible plastic. In an embodiment of the invention, the containment tubing can range in length from 10 millimeters to 10 meters. In an embodiment of the invention, the containment tubing can be made of nonwoven materials. In an embodiment of the invention, the containment tubing can be made from one or more woven materials.

In various embodiments of the invention, the one or more containment tubes can be hidden in any of these structural features. In various embodiments of the invention, the containment tube can be positioned within the container framework during construction of the container, including positioning of the one or more of the rails, stringers and reinforcing rings. The proximal end of the containment tube can exit the container framework so that the atmosphere at this location can be sampled. The distal end of the containment tube can exit the container framework and can be directed at the AISM. A vacuum can be employed to draw vapor from the regions of the container where the proximal end of the containment tube is positioned. The positions where the containment tubes exit the container framework can be concealed such that tampering with the containment tube can require detailed drawings or electronic sensors to locate the containment tube exit points. In addition, 'dummy' exit points can be introduced into the design to mask the location of real exit points. The 'dummy' exit points can hide the true exit location point and make tapering with the true exit points more problematic. The containment tube running throughout a portion of the container frame can also be concealed with foam. Foam can also be used as part of the container optimized insulation system. By disguising exit points, attempts to tamper with, restrict or otherwise block the containment tube can be minimized. By measuring the background in the container from a number of different points a more through examination of container content can be carried out. Measurement of the background can also be used to determine whether any of the containment tube exit points have undergone tampering.

Gas-Ion Separator (GIS)

In various embodiments of the invention, devices and methods for transferring analyte ions desorbed from the sorbent surface using an atmospheric analyzer into the inlet of a mass spectrometer can utilize a Gas-Ion Separator (GIS). Embodiments of this invention include devices and methods for collecting and transferring analyte ions and/or other analyte species formed within a carrier to the inlet of a mass spectrometer.

In an embodiment of the invention, one or both the inlet and the outlet GIS tubing can be made of one or more materials selected from the group consisting of stainless steel, non-magnetic stainless steel, steel, titanium, metal, flexible metal, ceramic, silica glass, plastic and flexible plastic. In an embodiment of the invention, the GIS tubing can range in length from 10 millimeters to 10 meters. In an embodiment of the invention, the GIS tubing can be made of non-woven materials. In an embodiment of the invention, the GIS tubing can be made from one or more woven materials.

In various embodiments of the invention, a GIS comprising two or more co-axial tubes with a gap between the tubes and a vacuum applied in the gap region is used to allow large volumes of carrier gas to be sampled. In various embodiments of the invention, a GIS is made up of an inlet tube and an outlet tube. In an embodiment of the invention, the proximal end of the inlet tube is closest to the sorbent surface and the distal end of the inlet tube can be some distance away from the proximal end where a vacuum can be applied. In various embodiments of the invention, the proximal end of the outlet tube is adjacent the distal end of the inlet tube and the distal end of the outlet tube enters the spectroscopy system. In various embodiments of the invention, by embedding the inlet tube in the container during construction of the container, the possibility of tampering with or otherwise interfering with the GIS can be reduced. A shipping container can include top, side and bottom rails with interval stringers in between the top and bottom rails and doors at one end. As many as 30 interval stringers can be present in a 40'. A shipping drum can contain reinforcing rings positioned at the bottom, one third, two thirds and top.

In various embodiments of the invention, a GIS inlet tube can be contained within the container framework including one or more of the rails, stringers, reinforcing rings and seams. The GIS inlet tube can be used to transfer ions formed at the sorbent surface to a spectroscopy system. The proximal end of the GIS inlet tube can exit the container framework to sample the ions formed at the sorbent surface. In various embodiments of the invention, the distal end of the GIS inlet tube can exit the container framework at a position to couple with the GIS outlet tube where a vacuum can be applied. In various embodiments of the invention, the distal end of the GIS inlet tube can exit the container framework at a site and couple with a second GIS inlet tube, wherein the GIS outlet tube and vacuum can be applied at a location distal to the site. The positions where the GIS inlet tube exits the container framework can be concealed such that tampering with the GIS inlet tube can require detailed drawings or electronic sensors to locate the GIS inlet tube exit points. In addition, 'dummy' GIS inlet tube exit points can be introduced into the design to mask the location of real exit points. The 'dummy' exit points can hide the true exit point location and make tampering with the true exit points more difficult. The GIS inlet tube running throughout a portion of the container frame can be concealed with foam. Foam can also be used as part of the container optimized insulation system. By disguising exit points, attempts to tamper with, restrict or otherwise block the GIS inlet tube can be minimized.

An atmospheric ionizer (such as DART®, DESI or other ambient pressure desorption ionization source) can generate ions at atmospheric pressure with the AISM sample surface at near ground potential. In an alternative configuration the sample surface can have an applied electric potential. As shown in FIG. 1 an atmospheric ionizer 100 can include the housing 103, an entry port 121 for introducing the carrier gas 122, an electrode 111 connected to a power supply 112 that supplies a potential difference between the electrode 111 and a counter electrode 147 that is sufficient to produce an electrical discharge which creates RS which subsequently pass and traverse through the length of the housing 103 through the exit grid 135 and thereby exit the atmospheric ionizer. In the case of desorption/ionization with an atmospheric ionizer there are situations in which there is no component of the system to which an electrical potential can be applied in order to selectively focus ions towards the mass spectrometer inlet. The process of desorption/ionization in these instances relies in large part on the action of the vacuum to draw the ions into the inlet of either the mass spectrometer (MS), ion mobility spectrometer (IMS) or differential mobility spectrometer (DMS).

Sorbent Material

Sampling inside confined spaces such as containers can involve capture of chemical containing atmosphere from the inside of the container and analysis of the captured atmosphere using appropriate chemical analysis techniques. Alternatively, the atmosphere can be sampled over a prolonged period by introducing a sorbent material into the confined space. Accordingly, the sorbent material can then be withdrawn outside the container and analysis carried out of the sorbent material using appropriate chemical analysis techniques. The chemical analysis can either be carried out on-site or sent to a remote laboratory for both identification and quantification of the threat posed by those chemicals prior to allowing the distribution of the contents of the confined space or the cargo of the container beyond the port area. However, these technologies suffer from the drawbacks that are resultant upon withdrawing a sample from the container and carrying out analysis of that sample. These drawbacks include the contamination of the sample subsequent to separation of the sample from the container, sample sabotage for example to cover narcotics interdiction efforts, sample tampering for example to cover illegal activity such as smuggling, increased background and increased probability of sampling error.

In an embodiment of the present invention, a sorbent material is used to sample the atmosphere within the confined space of a container over an interval of time. The sorbent material is subsequently subjected to analysis either while fixed in place in the container location or after removal from the container location. Analysis can include exposure of the sorbent material to a reactive species (RS) in order to ionize analyte species (AS) present on the sorbent material and transfer the AS to an analytical spectroscopy detection system.

In an embodiment of the invention, collection of chemical vapors for analysis in a confined space can be carried out by using a sorbent material such as but not limited to Tenax, silica gel, charcoal, alumina and more recently fullerenes. In various embodiments of the invention, a wide variety of chemical analysis methods can utilize various solvents to enable trace detection of substances of interest. In an alternative embodiment of the invention, sorbent materials can be chemically modified to permit enhanced capability for retention of specific analyte molecules or classes of chemicals thereby improving the potential for detection of those analyte molecules. In an embodiment of the invention, a sorbent material can be heat stable to permit reuse. In an alternative embodiment of the invention, a sorbent material can be consumed in the process of the analysis. In the case of desorption ionization at ambient pressure the sorbent material provides a substrate for the desorption ionization event when it is positioned at the distal end (i.e., in front) of the atmospheric ionizer or in contact with the gas exiting the atmospheric ionizer. In an embodiment of the invention, the sorbent material can be derivatized with a specific reactive group to react with specific analyte molecules of interest (e.g., reaction of surface impregnated potassium chloride with volatile nitrate to form nitrosyl chloride). In an alternative embodiment of the invention, the sorbent material can be derivatized with a reactive metal such as gold to form a reactive surface for a general analyte molecule of interest.

AISM

Figure 2A:
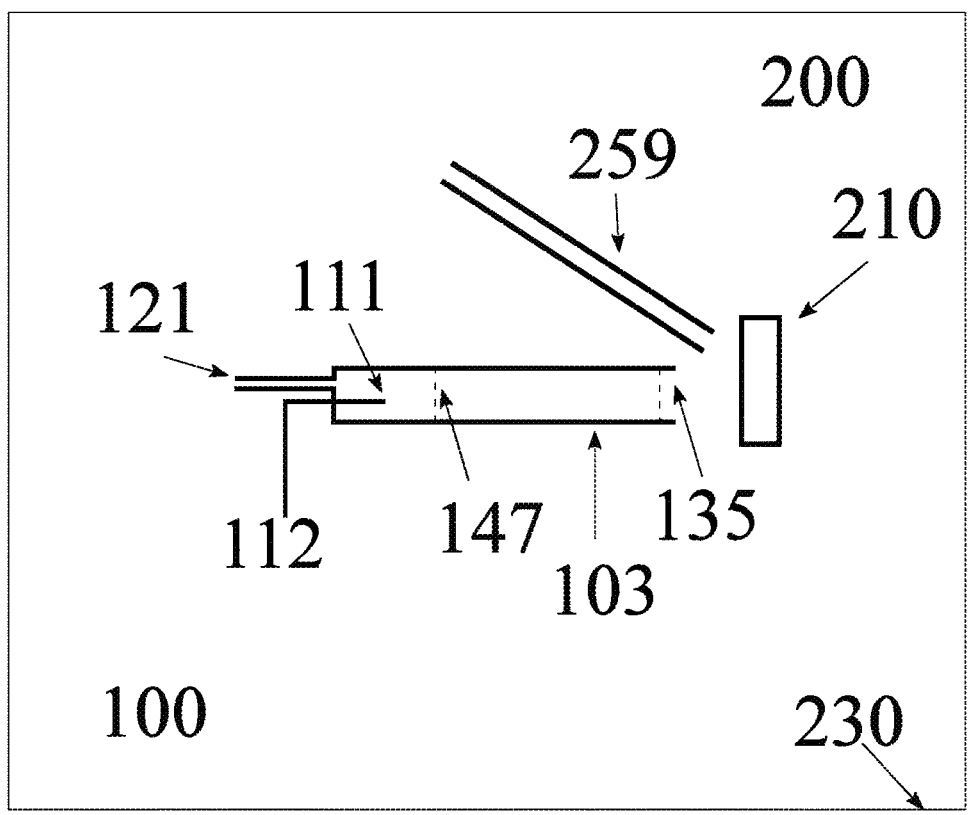
FIG. 2A is a schematic diagram of an embodiment of the invention with an atmospheric ionizer directed at an atmospheric ionizer sorbent material (atmosphere AISM) in which the entrance is open for collection of chemical traces, where the ionizer and AISM are located in a confined space of the container.
Figure 2B:
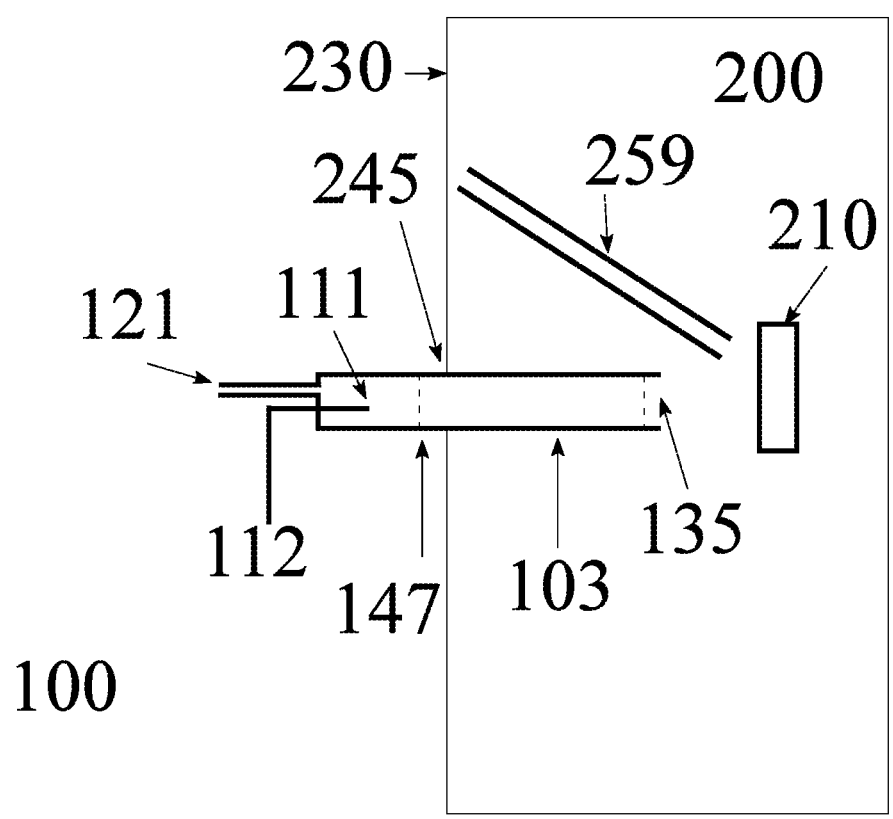
FIG. 2B is a schematic diagram of an embodiment of the invention where the AISM, but not the atmospheric ionizer is located in a confined space of the container.

In an embodiment of the invention, the combination of an atmospheric ionizer integrated with an Atmospheric Ionization Sorbent sampling Module (AISM) provides capability for rapid and long duration monitoring of container contents. As shown in FIG. 2A the AISM 200 includes a sorbent material 210 and a gas ion separator (inlet tube only is shown) 259 located inside the container. In an embodiment of the present invention, the AISM 200 can be positioned internal to the container 230 being analyzed. In an embodiment of the invention, an atmospheric ionizer 100 can also be positioned internal to the container 230 being analyzed. The atmospheric ionizer 100 includes a housing 103, an entry port 121, a power supply 112 that supplies a potential difference between the electrode 111 and a counter electrode 147 that is sufficient to produce an electrical discharge which creates RS which subsequently pass and traverse through the length of the housing 103 and after exiting the grid 135 are directed onto the sorbent material 210. In an alternative embodiment of the invention, as shown in FIG. 2B an atmospheric ionizer 100 can be positioned external to the container 230 while the sorbent material 210 and GIS 259 are within the container. The atmospheric ionizer 100 includes a housing 103, an entry port 121, a power supply 112 that supplies a potential difference between the electrode 111 and a counter electrode 147 that is sufficient to produce an electrical discharge which creates RS which subsequently pass and traverse through the length of the housing 103 and after exiting the grid 135 are directed onto the sorbent material 210 located inside the container 230. The atmospheric ionizer 100 passes thru the container at a hole or bung 245.

Figure 2C:
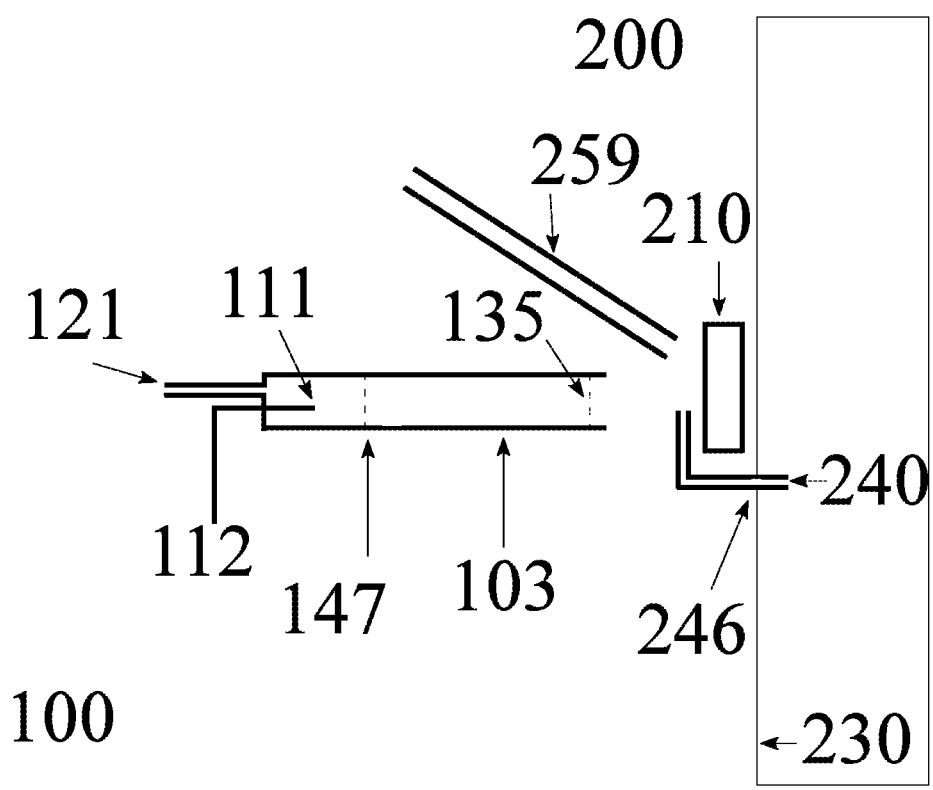
FIG. 2C is a schematic diagram of an embodiment of the invention where the AISM and the atmospheric ionizer are located outside the confined space of the container.

In another alternative embodiment of the present invention, shown in FIG. 2C the AISM 200 can be positioned external to the container 230 being analyzed. In this embodiment the sorbent material 210 and the inlet tube of a GIS 259 can be positioned outside of the container 230 (where one or both the AISM 200 and the sorbent material 210 can be isolated from the atmosphere, not shown in FIG. 2C). The atmosphere inside the container 230 can be introduced to the sorbent material 210 in the isolated atmosphere through a tube 240. In this embodiment, the atmospheric ionizer 100 can also be positioned external to the container 230 and directed onto the sorbent material 210. By positioning the AISM externally, 55-gallon drum containers and other size containers for shipping liquids can be monitored. By removing one of the bungs 246 on the top of the container 230 or through another entry point, the AISM can be connected through a tube 240 to the container 230. The AISM can remain attached to the container for a sufficient period of time in which the AISM monitors the contents. The atmospheric ionizer 100 includes a housing 103, an entry port 121, a power supply 112 that supplies a potential difference between the electrode 111 and a counter electrode 147 that is sufficient to produce an electrical discharge which creates RS which subsequently pass and traverse through the length of the housing 103 and after exiting the grid 135 are directed onto the sorbent material 210 located outside the container 230. The analyte species AS formed from molecules absorbed, adsorbed or condensed on the sorbent material 210 can then be directed into a spectrometer for analysis.

In an alternative embodiment of the invention, the AISM can be detached from the container and sent to a facility for analysis. At the facility the AISM is connected to the atmospheric ionizer 100 and an analyzer. The analyte species AS formed from molecules absorbed, adsorbed or condensed on the sorbent material 210 can then be directed into the spectrometer for analysis.

Figure 6:
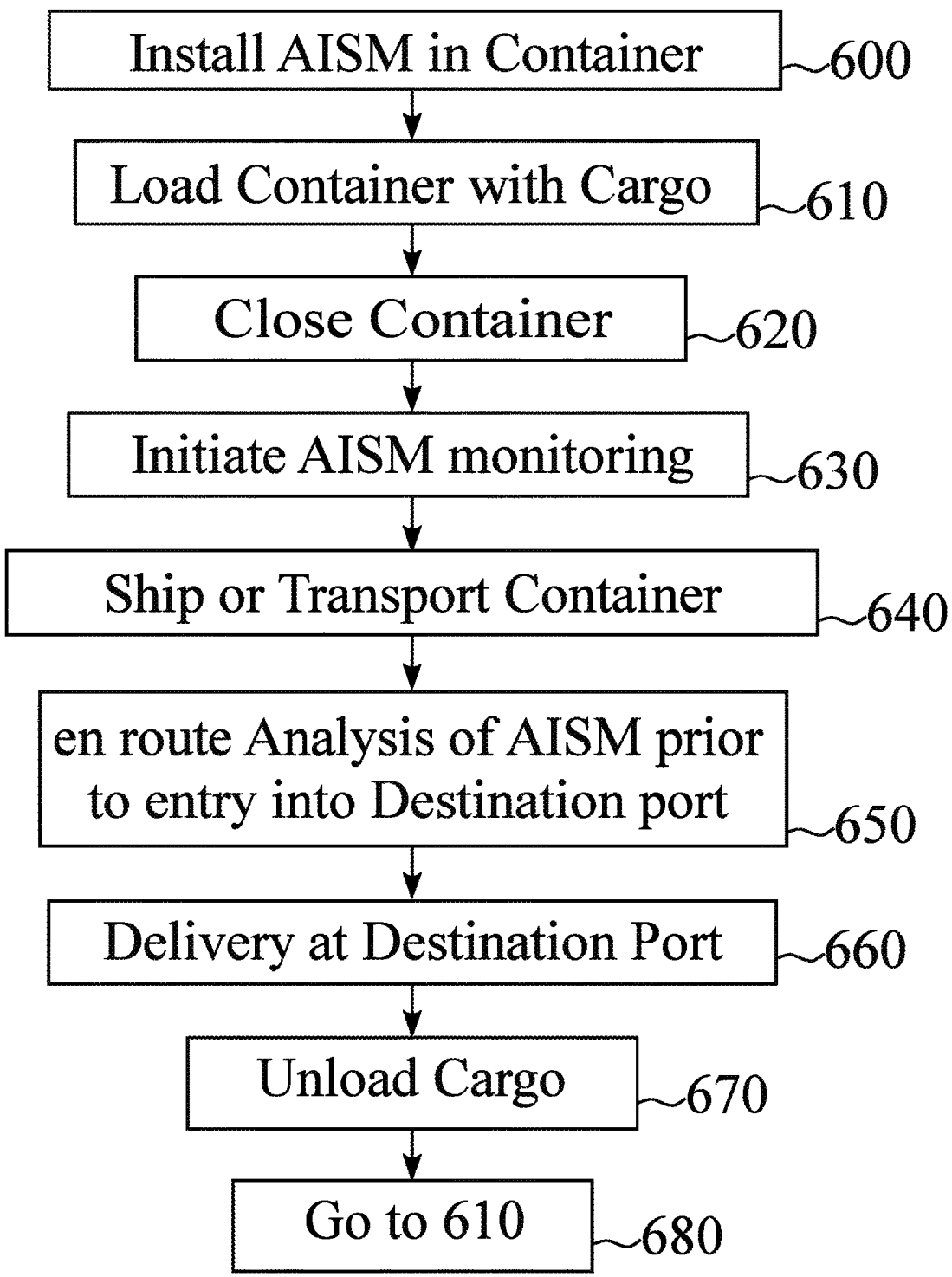
FIG. 6 is a flow diagram showing the use of an AISM installed in a cargo container according to an embodiment of the invention.

In an embodiment of the invention, AISM can provide for the rapid inspection of the container contents. In an embodiment of the invention, AISM can be operated robotically or in an automated fashion and without operator intervention to minimize operator exposure or danger to the contents of the container. In an embodiment of the invention, the AISM sorbent material can be in air contact or otherwise exposed to the internal contents of the container. In various embodiments of the invention, vapors can adsorb, absorb, condense or otherwise be captured on the sorbent material over time by controlling its temperature. In an alternative embodiment of the invention, internal tubing can be integrated into the container construction or otherwise utilized to allow collection of vapor from remote or segmented areas of the container. In an embodiment of the invention, a fan can be used to draw ambient air through the tubing so that it can be introduced to the headspace immediately adjacent to the sorbent material. In an embodiment of the invention, air can be re-circulated through the volume of the container. In an embodiment of the invention, the recirculation can provide for repetitive exposure of the sorbent to any volatile molecules associated with the container contents. As shown in FIG. 6, the AISM can be installed in (or on) a container 600. The cargo can already be loaded or subsequently be loaded onto the container 610. The door, opening or entry way for loading the cargo can then be closed 620. The monitoring using the AISM can then be initiated 630. Initiation can involve starting the fan to flow air through the container, unsealing or uncovering the sorbent material and/or regenerating the sorbent material. The cargo container is then shipped to a destination 640. Before reaching the destination, the AISM can be analyzed en route 650. Provided analysis reveals no restricted substance is present in the cargo, the cargo container is delivered to the destination 660. The cargo can then be unloaded from the container 670. The cargo container is then available for loading of a new cargo and shipment 680. The AISM can be replaced or regenerated to monitor the new cargo to be loaded.

Figure 3:
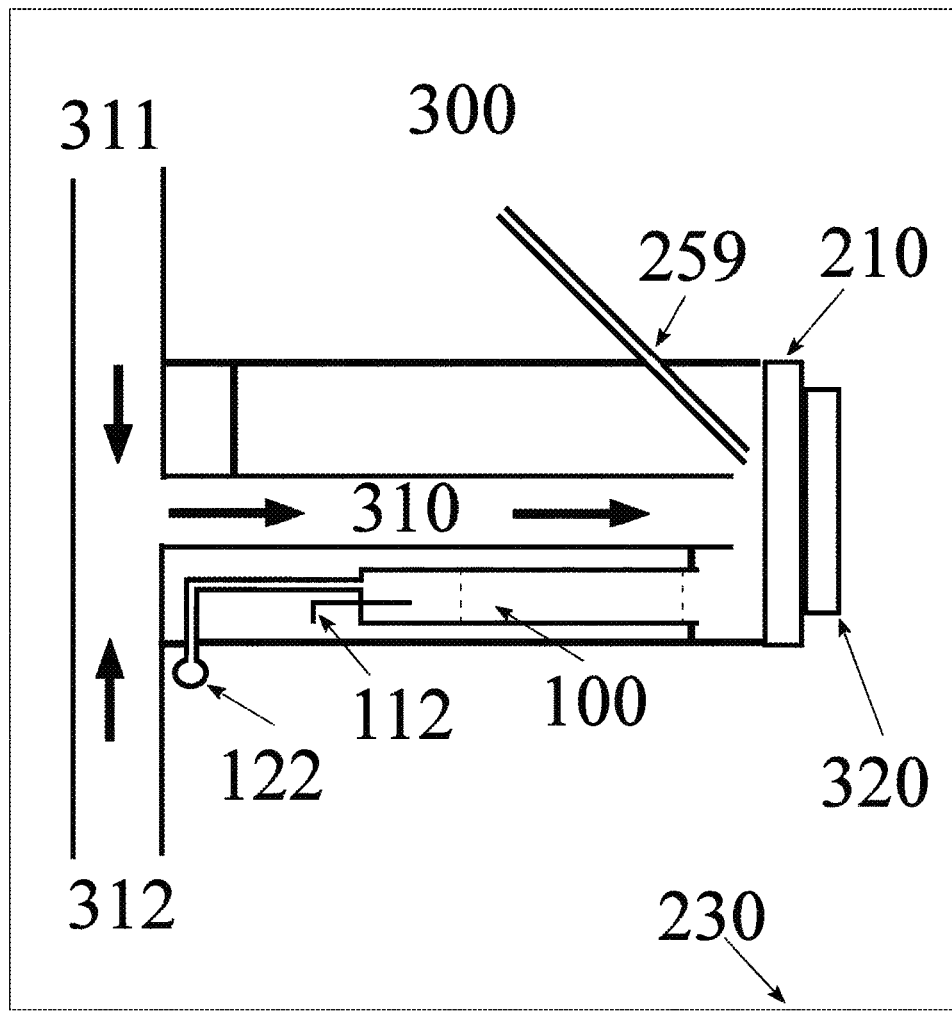
FIG. 3 is a schematic diagram of an embodiment of the invention with an atmospheric ionizer and an AISM where the ionizer and AISM are located in a container.

FIG. 3 shows an embodiment of the invention where the temperature of the sorbent material is controlled by a temperature controller 320. In an embodiment of the invention, the temperature controller 320 attached to the sorbent material 210 can be used to cryogenically cool the sorbent material in order to increase the condensation of molecules on the sorbent surface. In an alternative embodiment of the invention, the temperature controller 320 can heat the sorbent material 210 to effect desorption of condensed molecules from the sorbent. In an embodiment of the invention, by heating the sorbent material, adsorbed and/or absorbed molecules can be desorbed off the surface or from within the volume of the sorbent material for analysis. After analysis allowing the sorbent material to cool down in an inert environment results in the regeneration of the sorbent material 210, the AISM 300 can be reused. Alternatively, the AISM can be heated directly prior to use as an initiation step. Once the AISM has cooled down, it can begin collection. In an embodiment of the invention, the AISM 300 with regenerated sorbent material 210 can be used to continue monitoring or to begin monitoring the fresh contents of the container. Connecting pathways or tubes 310 allow the atmosphere in different regions 311, 312 of the containers to contact the sorbent material 210. In various embodiments of the invention, the AISM 300 with an atmospheric ionizer 100 includes an entry port for introducing the carrier gas 122, a power supply 112 that supplies a potential difference between electrodes to produce an electrical discharge and a GIS 259 (inlet tube only shown). The AISM 300 and atmospheric analyzer 100 can be positioned in the container housing by sliding the AISM 300 into a receptacle or port so that the distal end of the atmospheric ionizer 100 can introduce RS to the sorbent material 210. In such a configuration when the container is transported to a port of entry or is in transit to a port of entry, insertion of the AISM 300 attached to electrical and gas connections can be used to activate and analyze the sorbent material 210. In an alternative embodiment of the invention, when the container enters a port of entry the atmospheric ionizer and ancillary equipment are connected to the AISM 300 after removal of the AISM from the container.

Figure 4:
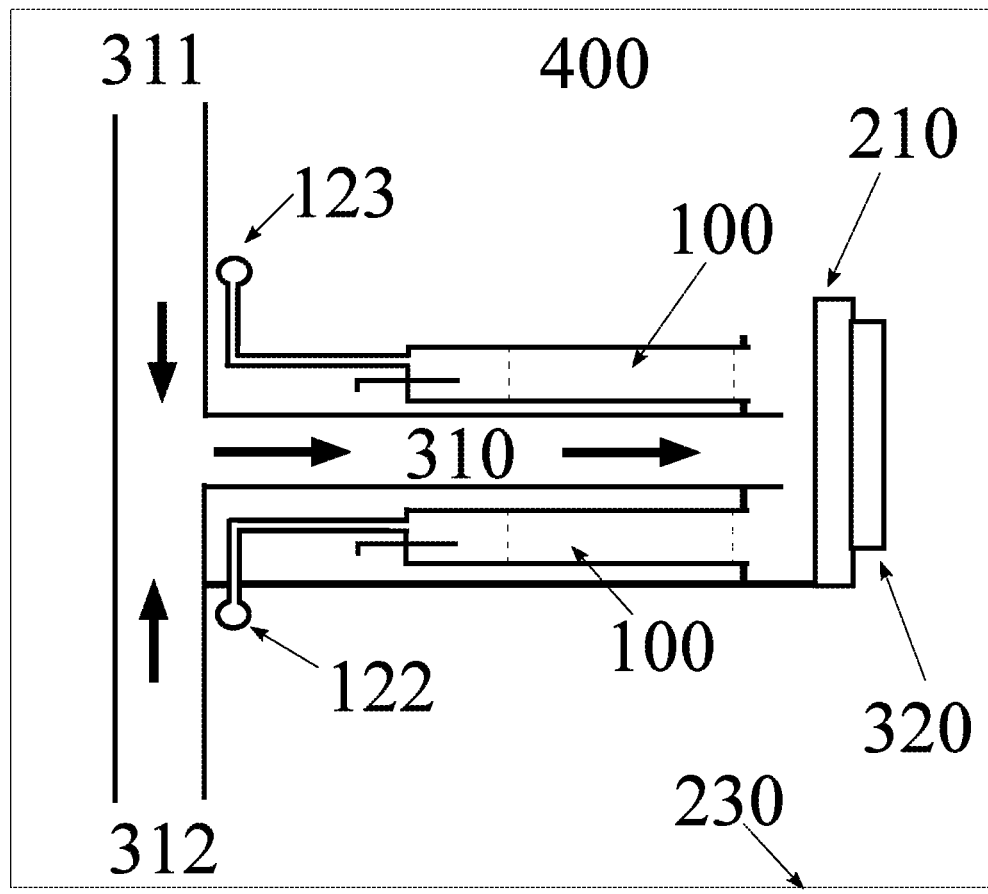
FIG. 4 is a schematic diagram of an embodiment of the invention showing an AISM which can be inserted into a container where the sorbent material is in contact with air in the container where multiple atmospheric ionizers can be directed at the sorbent material, where the multiple atmospheric ionizers and the AISM are located in a container.

FIG. 4 shows an embodiment of the invention where multiple atmospheric ionizers 100 are directed to the one or more sorbent material 210. Vapors from different regions of the container can be transported to the sorbent material through tube 310 which can be connected to a plurality of tubes the distal ends of which are open to the atmosphere thus permitting collection and transfer of atmospheric molecules from different regions of the container 311 and 312. The sorbent material 210 may be segmented into distinct regions each of which can be controlled by the temperature controller 320 which can also be segmented in order to provide the means to collect both low and high vapor pressure molecules from the same container for analysis. Multiple atmospheric ionizers 100 can be used in order to analyze different sections of the segmented sorbent material 210 with excited species generated at different temperatures or with different reagent species 122, 123. In an embodiment of the invention, a chemical signature is impregnated onto a sorbent material 210 as a means to confirm the integrity of the sorbent material 210. One or more of the multiple atmospheric ionizers 100 can be used in order to verify the integrity of the AISM module 300. Precise positional alignment between one or more atmospheric ionizers 100 and the GIS inlet tube can also be used to verify that the AISM 300 has not been tampered with or otherwise disabled. Precise positional alignment of one or more components of a chemical code in a chemical code pattern can be used to verify that the AISM 300 has not been tampered with or otherwise disabled.

In an embodiment of the invention, the AISM 300 is sealed to prevent exposure of the sorbent material 210 to ambient air during its transport or insertion into a container. In an embodiment of the invention, upon insertion into a container the AISM 300 is configured to permit exposure of the sorbent material 210 to the ambient atmosphere of the container thus beginning the sampling process. In an embodiment of the invention, the AISM 300 is designed to be placed in an enclosure embedded in the side of the container. In an alternative embodiment of the invention, the AISM 300 is designed to be suspended by a tether in a container. In another embodiment of the invention, the AISM 300 is designed to be fixed as an appendage in a container. In various other embodiments of the invention, the AISM 300 is otherwise configured in such a manner so as to permit the flow of gas from the container through a portion of the sampling module containing the sorbent material 210.

In an embodiment of the invention, during transport of the container it can be desirable to sample the contents of the container in a rapid manner without removing the AISM 300. In an embodiment of the invention, after transport of the container it can be desirable to sample the contents of the container in a rapid manner without removing the AISM 300. The advantage of sampling a container with robotic control or from a remote location is the interdiction of controlled substances before they pose an actual threat. By sampling a container ship on the high sea or at least before entry into port, explosive or lethal chemical biological and radiological threats can be addressed in a safer manner. The ability to expose different areas of an AISM 300 or different sorbent surfaces over time allows for compensation of background readings. The ability to sample from different compartments of a container onto different areas of an AISM 300 or different sorbent material 210 surfaces over time allows for analysis of the integrity of the whole system. Attempts to stop the flow of air from one compartment can be revealed by comparative analysis of that compartment with another compartment onto separate areas of an AISM 300 and/or comparison over time.

In an embodiment of the invention, radiological threats can be determined by using the GIS interface without turning on an atmospheric ionizer. The detection of analyte ions can be used to indicate the presence of alpha, beta or gamma irradiation. In an embodiment of the invention, reactive analyte molecules can be leaked into different compartments of a container to increase the probability of GIS detecting ionization and an analyzer thereafter analyzing analyte molecules. In an embodiment of the invention, water or ammonia gas or can be leaked into the container compartments and the detection of for example m/z 19 in the positive ionization mode or m/z 18 in the positive ionization mode or for example m/z 17 in the negative ionization mode or m/z 16 in the negative ionization mode can be use to identify a radiological threat.

In an embodiment of the invention, activation of the AISM for analysis can be facilitated by one or more of the following events (i) providing electrical power to the atmospheric ionizer; (ii) insertion of a subassembly that permits transfer of gas to the atmospheric ionizer (iii) enclosure of the sorbent material into a chamber. In an embodiment of the invention, enclosure of the sorbent in a chamber can be accompanied by introduction of a tube to permit transfer of analyte molecules together with carrier gas to a spectroscopy system. In an alternative embodiment of the invention, the spectroscopy system can be positioned in close proximity to the AISM for analysis at the container site. In another alternative embodiment of the invention, the spectroscopy system can be positioned in close proximity to the sampling tube for analysis at the container site. In another embodiment of the invention, the AISM can be removed within the chamber and transferred to a remote location for analysis. In another embodiment of the invention, the sorbent material can be removed from the chamber and transferred to a remote location for analysis.

In an embodiment of the invention, after analysis the AISM can be reactivated to allow for a subsequent analysis with the same sorbent surface. In another embodiment of the invention, the sorbent surface can be replaced to allow for a subsequent analysis with a new or regenerated sorbent surface. In an embodiment of the invention, a source of heat can be used to reactivate the sorbent surface. In an embodiment of the invention, heated gas from the atmospheric ionizer can be used to reactivate the sorbent surface. In an alternative embodiment of the invention, a thermoelectric source can be used to heat the sorbent surface. The heat acts at least by vaporizing residual chemical entities from the sorbent surface. In an embodiment of the invention, the reactivation of the sorbent surface enables multiple uses of the AIMS without requiring its removal from the container thus reducing operating cost. In an embodiment of the invention, a subassembly mates to the AIMS to effect the reactivation. In an embodiment of the invention, the reactivation can be carried out during insertion of the subassembly. In another embodiment of the invention, the reactivation can be completed after insertion of the subassembly. In an alternative embodiment of the invention, the reactivation can be carried out after the container is re-filled to reduce the possibility of false (negative or positive) indicators.

While external ion sources are known for use with MS, the problem of transporting sufficient ions to the MS typically results in lowered sensitivity. The problem is exacerbated with an external ionization source operated at or near atmospheric pressure, since the MS typically operates at high vacuum. In one embodiment of the invention, an atmospheric ionizer and a GIS deliver ions to the MS.

In various embodiments of the invention, a GIS comprising two or more co-axial tubes with a gap between the tubes and a vacuum applied in the gap region is used to allow large volumes of carrier gas to be sampled. In an embodiment of the invention, a GIS is made up of an inlet tube and an outlet tube where the proximal end of the inlet tube is closest to the atmospheric ionizer and the distal end of the inlet tube can be furthest from the atmospheric ionizer. The standard design of shipping containers can be an aide when designing a method of monitoring the contents of a shipping container. In various embodiments of the invention, the inlet tube can be assembled integral with the container during its construction, where the distal end of the inlet tube can be directed to the AISM and the proximal end of the inlet tube can be positioned adjacent to the spectroscopy system where the vacuum can be applied. In an embodiment of the invention, the outlet tube can be located within the spectroscopy system and can be used to one or both pre-concentrate and train the ions formed and flowing through the inlet tube of the gas ion separator to enter the spectroscopy system. In embodiments of the invention, by embedding the inlet tube in the container during construction of the container, the possibility of tampering with or otherwise interfering with the AISM detection system can be reduced.

B. Passive Ionization

In an embodiment of the invention, the same equipment used for active ionization can be used in a different conformation to analyze the contents of a container using passive ionization (i.e., requiring a radioactive nucleus to ionize the analyte molecules. In this experimental set up, the tube used to transport analyte molecules to the sorbent material can be used as an inlet tube of a GIS. The outlet tube would then be a separate tube positioned with an appropriate gap distance from this inlet tube. In an alternative embodiment of this invention, the function of the outlet tube would be performed by the active ionization inlet tube.

In various embodiments of the invention, the tube contained within the container framework including one or more of the rails, stringers, reinforcing rings and seams (hereinafter the contained tube), used to transfer the atmosphere at remote locations in the container to the area adjacent to the sorbent surface can also be used as an inlet tube for a GIS. The proximal end of the contained tube exits the container framework to sample a location in the container. The distal end of the contained tube exits the container framework at the position where the sorbent material is located. In this embodiment of the invention, the sorbent material is not utilized. The contained tube can act as an inlet tube for a GIS. By adjusting an outlet tube close to the distal end of the contained tube and applying a vacuum in this region, the outlet tube can one or both pre-concentrate and transfer ions formed at the location to a spectrometer. The region where the distal end of the contained tube exits near the sorbent material, and a vacuum can be applied is referred to as the Passive Ionization Module. By introducing an outlet tube connected to a spectroscopy system, where the outlet tube is adjusted to be in close proximity to the distal end of the contained tube and then introducing a vacuum to the region between the outlet tube and the distal end of the tube, the PIM can be converted into a GIS for sampling passive ionization occurring in distant locations in the container. In various embodiments of the invention, by using a GIS connected to these disparate locations in the container, the presence of ions can be used to infer that a radioactive nucleus is present in the container.

In an embodiment of the invention, a container adapted for detecting radioactive nuclei in the container comprises the container, wherein the container can be substantially confined on all sides, wherein the container includes at least a container distal end and a container proximal end, wherein the container proximal end has a first atmosphere, wherein the container distal end has a second atmosphere. A passive ionization module (PIM), wherein the PIM is adapted to receive a vacuum to be applied to a region in the PIM, wherein the PIM is adapted to receive an outlet tube connected to a spectroscopy system. Two tubes located in the container, wherein each of the two tubes have a distal end and a proximal end, wherein a distal end is located at the container distal end, wherein a distal end is located at the container proximal end, wherein the proximal end of the two tubes are located in the region in the PIM, wherein when the vacuum and the outlet tube connected to a spectroscopy system is received in the PIM the spectrometer detect ions formed in one or both the first atmosphere and the second atmosphere.

In an embodiment of the invention, a container adapted for detecting radioactive nuclei in the container comprises the container, wherein the container can be substantially confined on all sides, wherein the container includes at least a container distal end and a container proximal end, wherein the container proximal end has a first atmosphere, wherein the container distal end has a second atmosphere. A passive ionization module (PIM), wherein the PIM is adapted to receive a vacuum to be applied to a region in the PIM, wherein the PIM is adapted to receive an outlet tube, wherein the outlet tubes has a proximal end and a distal end, wherein the distal end of the outlet tube is connected to a spectroscopy system, wherein the proximal end of the outlet tube is located in the regions in the PIM. One or more tubes located in the container, wherein each of the one or more tubes have a distal end and a proximal end, wherein the distal end of the one or more tubes is located at one or both the container distal end and the container proximal end, wherein the proximal end of the one or more tubes is located in the region in the PIM, wherein when the vacuum and the outlet tube connected to a spectroscopy system is received in the PIM the spectroscopy system detects ions formed in one or both the first atmosphere and the second atmosphere.

In an embodiment of the invention, a container adapted for detecting radioactive nuclei in the container comprises the container, wherein the container can be substantially confined on all sides, wherein the container includes at least a container distal end and a container proximal end, wherein the container proximal end has a first atmosphere, wherein the container distal end has a second atmosphere. One or more passive ionization modules (PIMs), wherein each of the one or more PIMs is adapted to receive a vacuum to be applied to one or more regions in the one or more PIMs, wherein each of the one or more PIMs is adapted to receive one or more outlet tubes, wherein each of the one or more outlet tubes has a proximal end and a distal end, wherein the distal end of the one or more outlet tubes is connected to one or more spectroscopy systems, wherein the proximal end of the one or more outlet tubes is located in the one or more regions in the one or more PIMs. One or more tubes located in the container, wherein each of the one or more tubes have a distal end and a proximal end, wherein the distal end of the one or more tubes is located at one or both the container distal end and the container proximal end, wherein the proximal end of the one or more tubes is located in the one or more regions in the PIMs, wherein when the vacuum and the outlet tube connected to a spectroscopy system is received in the one or more PIMs the one or more spectroscopy systems detect ions formed in one or both the first atmosphere and the second atmosphere.

A method for detecting the presence of a controlled substance in a container, comprises receiving the container including one or more atmospheric ionization sorbent modules (AISM) containing one or more sorbent surfaces and one or more regions in front of the sorbent surfaces, wherein the one or more AISM are located one or both within the container and outside the container, wherein the one or more AISM are adapted to receive one or more atmospheric ionizers and one or more tubes located in the container connecting one or both the distal end and the proximal end to the region in front of the sorbent surface. Coupling one or more atmospheric ionizer with the one or more AISM, wherein the one or more atmospheric ionizers are directed at the one or more regions in front of the sorbent surface, wherein the one or more atmospheric ionizers form ions of molecules present in one or both the one or more regions in front of the one or more sorbent surfaces and on the one or more sorbent surfaces. Connecting one or more gas ion separator (GIS) in the one or more regions in front of the sorbent surfaces, wherein the one or more AISM are adapted to receive the one or more GIS. Connecting one or more spectrometers to the one or more GIS, wherein the one or more GIS transport the ions into the one or more spectroscopy system. Detecting the ions to determine the presence of a controlled substance.

In another embodiment of the invention, a Radio Frequency IDentification (RFID) tag is imbedded in one or more AISM. In one embodiment of the invention, the RFID tag operates using an Ultra High Frequency (UHF) signal. In another embodiment of the invention, the RFID tag operates using a microwave frequency signal. In an embodiment the RFID tag can be positioned so that the RFID tag antenna is least affected by surrounding metal.

In one embodiment the RFID tag is read only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi passive containing a source of energy such as a battery to allow the tag to be constantly powered. In a further embodiment of the invention, the RFID tag is active, containing an internal power source, such as a battery, which is used to power any Integrated Circuit's (ICs) in the tag and generate the outgoing signal. In another embodiment, the tag has the ability to enable location sensing through a photo sensor.

In one embodiment of the invention, a cellular modem is imbedded in the AISM. The cellular modem can be a Code Division Multiple Access (CDMA) modem. In an embodiment of the invention, a RFID reader and associate integrated circuit processor are embedded together with the cellular modem in the AISM. In such an embodiment, the RFID tags and RFID reader are positioned to optimize the RFID read of the RFID tags from the other AISM in the container.

In an embodiment of the invention, where a RFID reader and a cellular modem are embedded in the core of one or more of the AISM, the RFID reader is in communication with one or more of the RFID tags of AISM in the vicinity of the RFID reader. In an embodiment of the invention, the RFID reader and associate processor are in communication with the embedded cellular modem. In an embodiment of the invention, the cellular modem is in communication with a base station and can transmit one or more parameters selected from the group consisting of one or more RFID tag location, one or more RFID tag identification code, shipment information, analysis information, duration of analysis and time stamp.

In an embodiment of the invention, the microprocessor that monitors the integrity of the shipping container can transmit an alarm signal through the cellular modem thereby silently alerting the shipping agent to the identity of the contents.

In one embodiment of the invention the RFID code uses the IEEE format and is Electronic Product Code (EPC) readable. In another embodiment of the invention the RFID code uses the UCC format and is Universal Product Code (UPC) readable. In another embodiment, the format is compatible for EPC, European Article Number (EAN) and UPC read and write functions.

A system for determining the presence of controlled substances when transporting a cargo for a period of time comprising receiving a container for holding the cargo, wherein the container can be substantially confined on all sides, wherein the container includes one or more sorbent surface located inside the container, wherein the one or more sorbent surface is exposed to the atmosphere inside the container for at least a portion of the period of time. One or more atmospheric ionizer located in the container, wherein the atmospheric ionizer produces reactive species, wherein the reactive species are directed onto one or more sorbent surface. One or more gas ion separators located in the container to transfer analyte ions formed off the sorbent surface into a spectrometer for one or more analysis. One or more spectrometers located in the container for detecting analyte ions. Receiving analysis data from the one or more spectrometer. Correlating the analysis data with analysis of controlled substances, wherein the correlating can also involve one or more parameters selected from the group consisting of the period of time and the portion of the period of time the sorbent material is exposed.

A system for determining the presence of controlled substances when transporting a cargo for a period of time comprising receiving a container for holding the cargo, wherein the container can be substantially confined on all sides, wherein the container includes one or more sorbent surface located inside the container, wherein the one or more sorbent surface is exposed to the atmosphere inside the container for at least a portion of the period of time. One or more gas ion separators inlet tubes. Receiving an AISM ionizer/analyzer, wherein the AISM ionizer/analyzer can be located to sample the sorbent surface located in the container including one or more atmospheric ionizer wherein the atmospheric ionizer produce reactive species, wherein the reactive species are directed onto one or more sorbent surface. One or more gas ion separators outlet tubes. A spectrometer for detecting analyte ions, wherein the one or more gas ion separator inlet tube located in the container and the one or more gas ion separator outlet tube connect to transfer analyte ions formed off the sorbent surface into the spectrometer for one or more analysis. Receiving analysis data from the AISM ionizer/analyzer. Correlating the analysis data with analysis of controlled substances, wherein the correlating can also involve one or more parameters selected from the group consisting of the period of time and the portion of the period of time the sorbent material is exposed.

The system for determining the presence of controlled substances when transporting a cargo for a period of time wherein reactive species from at least one atmospheric ionizer are directed onto one sorbent surface.

The system for determining the presence of controlled substances when transporting a cargo for a period of time wherein two or more sorbent surfaces undergo spectrometric analysis to sample different compartments within the container.

The system for determining the presence of controlled substances when transporting a cargo for a period of time, wherein two or more sorbent surfaces are analyzed to provide an average analysis representative of the contents of the container.

The system for determining the presence of controlled substances when transporting a cargo for a period of time wherein two or more sorbent surfaces are analyzed to provide analysis from different compartments with the container.

The system for determining the presence of controlled substances when transporting a cargo for a period of time wherein the sorbent surface also contains a chemical code to verify the integrity of the sorbent surface. The chemical code can be one or more molecules that are stable to oxidation or stable to further oxidation and have sufficiently low vapor pressure that they remain present on the sorbent surface after deposition for a period of approximately 12 months. The chemical code can be one or more molecules that do not produce ions that can interfere with the analysis of common controlled substances including explosives, radiation threats or illicit drugs. The chemical code can include one or more polydisperse or monodisperse synthetic organic polymers, paints, dyes, other small (less than approximately 200 Dalton) organic molecules and other small (less than approximately 200 Dalton) inorganic molecules. In an embodiment of the invention, the synthetic polymers include polyether, polyglycol, polyester, polyethylene, poly(halogen)ethylene, polypropylene, polyvinylidene halogen, polymethylmethacrylate, polyacrylonide, polycaprolactone, polylactide, poly butylene succinate, polybutylene succinate adipate, polybutylene succinate terephthalate, poly-hydroxypropionate, poly-hydroxybutyrate, poly-hydroxyvalerate, poly-hydroxyhexanoate, poly-3-hydroxyoctanoate, poly-3-hydroxyphenylvaleric acid and poly-3-hydroxyphenylhexanoic acid. In an embodiment of the invention, the dyes can include one or more dyes selected from the group consisting of methoxycoumarin, coumarins, fluorescein, bodipy-Fl, ethidium bromide, bodipy-R6G, Rhodamine, TAMRA, Cy-3 and Coomassie blue. In an embodiment of the invention, the inorganic molecules include transition metal oxides including FeS, NiO, $SiO_2$, $Ni_2O_3$, $Al_2O_3$, $Fe_2O_3$ and $Fe_3O_4$. In an embodiment of the invention, the chemical code is a (0.5:0.01:1:0.1, wt:wt) mixture of monodisperse polystyrene (n=4), Coomassie blue, fructose and $Fe_2O_3$. The chemical code can be arranged in a specific pattern on the sorbent surface. The pattern can be in the form of a bar code so that the chemical code functions as both a chemical and physical bar code. In an embodiment of the invention, an appropriate wavelength light can be used to scan the sorbent material and a dye which makes up the chemical code can be used to verify the presence of the chemical code on the sorbent surface without the need to use the spectroscopy system. The system for determining the presence of controlled substances when transporting a cargo for a period of time containing a sorbent surface with a chemical code wherein reactive species from at least one atmospheric ionizer are directed onto the chemical code of the sorbent surface to verify the integrity of the sorbent surface.

The system for determining the presence of controlled substances when transporting a cargo for a period of time wherein two or more sorbent surfaces are exposed for different portions of the period of time. The system for determining the presence of controlled substances when transporting a cargo for a period of time, two or more sorbent surfaces are exposed for different portions of the period of time, wherein the two or more sorbent surfaces undergo spectrometric analysis and the two or more analyses are correlated with the different portions of the period of time to verify the analysis.

The system for determining the presence of controlled substances when transporting a cargo for a period of time wherein the temperature of one or more of the sorbent surfaces is held for at least a portion of the period of time at between a lower limit of approximately $1 \times 10^2$ degrees K and an upper limit of approximately $4 \times 10^2$ degrees K.

The system for determining the presence of controlled substances when transporting a cargo for a period of time wherein one or more of the sorbent surfaces is regenerated by heating to between a lower limit of approximately $3 \times 10^2$ degrees K and an upper limit of approximately $5 \times 10^2$ degrees K.

The system for determining the presence of controlled substances when transporting a cargo for a period of time wherein one or more of the atmospheric ionizer is activated by connection to two or more utilities selected from the group consisting of a source of electrical current, a pressurized volume of gas of between a lower limit of approximately 2 kPa and an upper limit of 60 kPa and a vacuum pump capable of generating a vacuum between a lower limit of approximately 10 torr and an upper limit of approximately 500 torr.

The system for determining the presence of controlled substances when transporting a cargo for a period of time wherein the spectrometer is selected from the group consisting of an ion mobility spectrometer, a mass spectrometer, an infrared spectrometer, a differential mobility spectrometer, a digital mass spectrometer and a chemical analyzer.

A cargo container detection system that comprising a cargo container. One or more atmospheric ionizer, capable of producing reactive species (RS), wherein one or more of the atmospheric ionizer include a vessel with an outlet where the RS exit, wherein the one or more atmospheric ionizer are locatable to one or more regions in the container, wherein the plurality of RS that exit the distal tube of the atmospheric ionizer interact and ionize analyte species (AS) present in the container. One our more gas ion separators (GIS) locatable within the container, wherein the plurality of AS enter the proximal end of one or more GIS inlet tube and exit the distal end of the GIS inlet tube, wherein the plurality of AS enter the proximal end of one or more GIS outlet tube and exit the distal end of the GIS outlet tube. One or more spectrometer for analysis, wherein the one or more spectrometer are locatable to one or more locations, wherein the plurality of AS that exit the distal end of the GIS outlet tube enter the one or more spectrometer, wherein the AS are detected in the one or more spectrometer.

The cargo container detection system wherein one or more atmospheric ionizer is positioned a distance from the proximal end of one or more GIS inlet tube between a lower limit of approximately $1 \times 10^{-6}$ m and an upper limit of approximately $3 \times 10^{-2}$ m.

The cargo container detection system wherein the distal end of one or more GIS inlet tube is positioned a distance from the vacuum region associated with the one or more spectrometer between a lower limit of approximately $1 \times 10^{-6}$ m and an upper limit of approximately $1 \times 10^{-2}$ m.

The cargo container detection system wherein the one or more atmospheric ionizer regions are approximately coincident with the one or more spectrometer locations.

The cargo container detection system wherein the air in the container is one or both blown and sucked from one or more regions within the container in to the region around one or more atmospheric ionizer.

The cargo container detection system wherein the RS pass thru one or more RS tubes, wherein the RS tube has a distal and a proximal end, wherein the RS enter the proximal end and exit the distal end before interacting and ionizing an analyte molecule.

The cargo container detection system the RS pass thru one or more RS tubes, wherein one or both the RS tubes and the GIS inlet tubes are built into the substructure of the cargo container.

The cargo container detection system the RS pass thru one or more RS tubes, wherein one or both the RS tubes and the GIS inlet tubes are not accessible from inside the container and outside the container.

The cargo container detection system the RS pass thru one or more RS tubes, wherein a sorbent surface is placed at the distal end of the RS tubes, wherein the RS exiting the distal end of the RS tubes impinge on the sorbent surface.

The cargo container detection system wherein a sorbent surface is placed at the distal end of the RS tubes, wherein means for one or both blowing and sucking air is used to recirculate air from one or more regions within the container across the sorbent surface.

The cargo container detection system wherein a sorbent surface is placed at the distal end of the RS tubes, wherein the one or more distal end of RS tubes are located in close proximity to one or more sorbent surfaces sufficient to produce one or more AS for detection.

A method for detecting the presence of one or more controlled substances in a transport container, comprising receiving the container after transport of the container, wherein one or more atmospheric ionization sorbent module (AISM) was installed one or both prior to and during transport of the container. Locating one or more atmospheric ionizer on or near the container, wherein the atmospheric ionizer is located such that a plurality of reactive species from the one or more atmospheric ionizer impinge the one or more AISM, wherein a plurality of analyte species are formed when the reactive species impinge the one or more AISM. Locating one or more spectrometers on or near the container, wherein the one or more spectrometers are located such that a plurality of analyte species formed at the one or more AISM enter the one or more spectrometers. Detecting the analyte species with the one or more spectrometers to determine if one or more controlled substances were present in the container.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exemplary embodiments, but should be defined only in accordance with the following claims and their equivalents.

What is claimed is:

1. A cargo monitoring system comprising:
   (a) receiving a container with an atmosphere, where the container is adapted to detachably attach an atmospheric ionization sorbent module (AISM) including a sorbent material;
   (b) attaching the AISM to the container;
   (c) directing a flow of the atmosphere onto the AISM to transfer one or more analyte molecules in the atmosphere to the sorbent material;
   (d) directing ionizing species from an atmospheric ionizer at the sorbent material to generate one or more analyte ions; and
   (e) analyzing the one or more analyte ions with a spectrometer.

2. The cargo monitoring system of claim 1, where the one or more analyte molecules can be absorbed, adsorbed or condensed on the sorbent material.

3. The cargo monitoring system of claim 1, where movement of the atmosphere within the container to the sorbent material is facilitated.

4. The cargo monitoring system of claim 1, where the atmosphere is directed to the sorbent material over an interval of time.

5. The cargo monitoring system of claim 1, where the sorbent material is subjected to analysis in situ.

6. The cargo monitoring system of claim 1, where the sorbent material is subjected to analysis after detaching the AISM from the container.

7. The cargo monitoring system of claim 1, further comprising detaching the AISM from the container prior to step (d).

8. The cargo monitoring system of claim 1, further comprising transferring the one or more analyte ions to the spectrometer for analysis in step (e).

9. The cargo monitoring system of claim 1, where the ionizing species are directed towards a surface of the sorbent material to generate the one or more analyte ions.

10. The cargo monitoring system of claim 9, where the one or more analyte ions are transferred from the surface to the spectrometer for analysis.

11. A method of identifying one or more controlled substances in a shipping container, comprising:
    (a) receiving a shipping container with an atmosphere;
    (b) attaching an atmospheric ionization sorbent module (AISM) with a sorbent surface to the shipping container;
    (c) directing a flow of the atmosphere onto the AISM to transfer one or more analyte molecules in the atmosphere to the sorbent surface;
    (d) detaching the AISM from the shipping container;
    (e) directing ionizing species from an atmospheric ionizer at the sorbent surface to generate one or more analyte ions; and
    (f) analyzing the one or more analyte ions with a spectrometer to determine if one or more controlled substances are present in the shipping container.

12. The method of claim 11, where the one or more analyte molecules can be absorbed, adsorbed or condensed on the sorbent surface.

13. The method of claim 11, where movement of the atmosphere within the shipping container to the sorbent surface is facilitated.

14. The method of claim 11, where the atmosphere is directed to the sorbent surface over an interval of time.

15. An atmospheric ionization sorbent module (AISM) comprising:
    (a) a housing with a proximal end and a distal end;
    (b) a tube with an inlet and an outlet positioned at the distal end;
    (c) a connector for attaching the inlet to a connecting pathway on a cargo container;
    (d) a sorbent material positioned in proximity to the outlet at the distal end;
    (e) a fan for recirculating air from one or more regions within the cargo container through the connecting pathway to the inlet to transfer one or more analyte molecules through the outlet to the sorbent material; and
    (f) means for releasing the connector to detach the AISM from the cargo container for analysis of the one or more analyte molecules transferred to the sorbent material.

16. The AISM of claim 15, where the sorbent material is segmented into distinct regions.

17. The AISM of claim 15, further comprising a chemical code impregnated onto the sorbent material.

18. The AISM of claim 15, further comprising a temperature controller to control the temperature of the sorbent material.

19. The AISM of claim 15, further comprising: an entry port for a carrier gas, a power supply that supplies a potential difference between an electrode and a counter electrode to produce an electrical discharge which creates reactive species which subsequently pass and traverse through the length of the housing directed onto the sorbent material.

20. The AISM of claim 19, further comprising a gas ion separator to analyze species formed by the reactive species directed onto the sorbent material.

* * * * *